US008829190B2

(12) United States Patent
Felding et al.

(10) Patent No.: US 8,829,190 B2
(45) Date of Patent: Sep. 9, 2014

(54) TRIAZOLOPYRIDINES AS PHOSPHODIESTERASE INHIBITORS FOR TREATMENT OF DERMAL DISEASES

(75) Inventors: Jakob Felding, Charlottenlund (DK); Morten Dahl Sørensen, Hørsholm (DK)

(73) Assignee: Leo Pharma A/S, Ballerup (DK)

( * ) Notice: Subject to any disclaimer, the term of this patent is extended or adjusted under 35 U.S.C. 154(b) by 695 days.

(21) Appl. No.: 12/595,922

(22) PCT Filed: Apr. 16, 2008

(86) PCT No.: PCT/DK2008/000135
§ 371 (c)(1),
(2), (4) Date: Oct. 14, 2009

(87) PCT Pub. No.: WO2008/125111
PCT Pub. Date: Oct. 23, 2008

(65) Prior Publication Data
US 2010/0113442 A1 May 6, 2010

Related U.S. Application Data

(60) Provisional application No. 60/912,020, filed on Apr. 16, 2007.

(51) Int. Cl.
*C07D 471/04* (2006.01)
*A61K 31/437* (2006.01)

(52) U.S. Cl.
CPC ............ *C07D 471/04* (2013.01); *A61K 31/437* (2013.01)
USPC .......................................... 546/120; 514/303

(58) Field of Classification Search
CPC ........................... C07D 471/04; A61K 31/437
USPC .......................................... 546/120; 514/303
See application file for complete search history.

(56) References Cited

U.S. PATENT DOCUMENTS 6,303,600 B1 * 10/2001 Cox et al. ................... 514/235.5

FOREIGN PATENT DOCUMENTS

WO WO-2004/072072 A1 8/2004
WO WO-2006/038116 A2 4/2006

OTHER PUBLICATIONS

Michalski et. al. "PDE4: A Novel Target in the Treatment of Chronic Obstructive Pulmonary Disease" Clinical pharmacology & Therapeutics 2012, 91(1), 134-142.*

Simone, Oncology: Introduction, Cecil Textbook of Medicine, 20th Edition, 1996 vol. 1, pp. 1004-1010.*
Trisha Gura "Cancer Models: Systems for Identifying New Drugs Are Often Faulty" Science Nov. 7, 1997: vol. 278. No. 5340, pp. 1041-1042.*
Regan, John et. al. "2-Substituted 4-methoxybenzimidazole-based PDE4 inhibitors." Bioorganic & Medicinal Chemistry Letters, 1998, 8(19), 2737-2742.*
George A. Patani "Bioisosterism: A Rational Approach in Drug Design" Chemical Reviews 1996, 96, 3147-3176.*
Wermuth, Camille G. "Molecular Variation Based on Isosteric Replacements" in Chapter 13, The Practice of Medicinal Chemistry, Academic: 1996, 203-237.*
West, Anthony R., Solid State Chemistry and its Applications, Wiley, New York, 1988, pp. 358 & 365.*
Brodbeck, Bernd, et al. "Parallel iterative solution-phase synthesis of 5-amino-1-aryl-[1,2,4]triazolo[1,5-a] pyridine-7carboxylic acid amide derivatives" Tetrahedron Letters, Science Direct No. 44, 2003, pp. 1675-1678.

* cited by examiner

*Primary Examiner* — David K O Dell
(74) *Attorney, Agent, or Firm* — Birch Stewart, Kolasch & Birch, LLP

(57) ABSTRACT

The present invention relates to a compound according to formula (I), wherein X and Y are either C and N or N and C; Z is $CH_2$, $CH_2$—$CH_2$, $CH_2$—NH, or NH; $R_1$ is halogen, or $R_1$ is alkyl, alkenyl, alkynyl, haloalkyl, alkoxy, cycloalkyl, alkoxycarbonyl, aryl, all of which are optionally substituted; $R_2$ is hydrogen, or $R_2$ is alkyl, cycloalkyl, alkoxy, heterocycloalkyl, aryl, heteroaryl, alkoxycarbonyl, aminocarbonyl, amino, all of which are optionally substituted; A is aryl, cycloalkyl, cycloalkenyl, heteroaryl, heterocycloalkyl or heterocycloalkenyl, all of which are optionally substituted; and pharmaceutically acceptable salts, hydrates, or solvates hereof. The invention further relates to said compounds for use in therapy, to pharmaceutical compositions comprising said compounds, to methods of treating diseases, e.g. dermal diseases, with said compounds, and to the use of said compounds in the manufacture of medicaments, in particular for the treatment of dermal diseases.

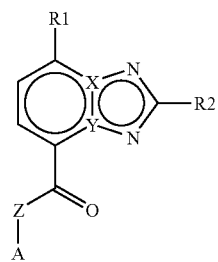

13 Claims, No Drawings

TRIAZOLOPYRIDINES AS PHOSPHODIESTERASE INHIBITORS FOR TREATMENT OF DERMAL DISEASES

This application is the National Phase of PCT/DK2008/000135 filed on Apr. 16, 2008, which claims priority under 35 U.S.C. 119(e) to U.S. Provisional Application No. 60/912,020 filed on Apr. 16, 2007, all of which are hereby expressly incorporated by reference into the present application.

FIELD OF THE INVENTION

The present invention relates to novel compounds with phosphodiesterase inhibitory activity, as well as to their use as therapeutic agents in the treatment of inflammatory diseases and conditions.

BACKGROUND OF THE INVENTION

Phosphodiesterases are enzymes that catalyse the hydrolysis of cyclic AMP and/or cyclic GMP in cells to 5-AMP and 5-GMP, respectively, and as such they are critical to cellular regulation of cAMP or cGMP levels. Of the 11 phosphodiesterases identified so far, phosphodiesterase (PDE) 4, PDE7 and PDE8 are selective for cAMP. PDE4 is the most important modulator of cAMP expressed in immune and inflammatory cells such as neutrophils, macrophages and T-lymphocytes (Z. Huang and J. A. Mancini, *Current Med. Chem.* 13, 2006, pp. 3253-3262). As cAMP is a key second messenger in the modulation of inflammatory responses, PDE4 has been found to regulate inflammatory responses of inflammatory cells by modulating proinflammatory cytokines such as TNFα, IL-2, IFN-γ, GM-CSF and LTB4. Inhibition of PDE4 has therefore become an attractive target for the therapy of inflammatory diseases such as asthma, chronic obstructive pulmonary disease (COPD), rheumatoid arthritis, atopic dermatitis, inflammatory bowel disease such as Crohn's disease etc. (M. D. Houslay et al., *Drug Discovery Today* 10 (22), 2005, pp. 1503-1519). As atopic dermatitis (AD) patients have increased PDE-activity, PDE4-inhibition would also appear to be a viable treatment of AD (Journal of Investigative Dermatology (1986), 87(3), 372-6).

The PDE4 gene family consists at least of four genes, A, B, C and D, which have a high degree of homology (V. Boswell Smith and D. Spina, *Curr. Opinion Investig. Drugs* 6(11), 2006, pp. 1136-1141). The four PDE4 isoforms are differentially expressed in different tissues and cell types. Thus, PDE4B is predominantly expressed in monocytes and neutrophils, but not in cortex and epithelial cells, while PDE4D is expressed in lung, cortex, cerebellum and T-cells (C. Kroegel and M. Foerster, *Exp. Opinion Investig. Drugs* 16(1), 2007, pp. 109-124). It has been speculated that inhibition of PDE4D in the brain is associated with the adverse effects found when administering PDE4 inhibitors clinically, primarily nausea and emesis, whereas inhibition of PDE4B is associated with anti-inflammatory effects (B. Lipworth, *Lancet* 365, 2005, pp. 167-175). However, the PDE inhibitors developed so far are not believed to be specific for any of the four PDE4 isoforms.

Numerous PDE4 inhibitors have been studied for their therapeutic effect on inflammatory diseases, primarily asthma and COPD.

The first of these, theophylline, is a weak, non-selective phosphodiesterase inhibitor used in the treatment of respiratory diseases such as asthma and COPD. Treatment with theophylline may, however, give rise to both mild and severe adverse effects, e.g. arrhythmia and convulsions, restricting the clinical utility of theophylline (Kroegel and Foerster, supra). As phosphodiesterase has remained an attractive target for anti-inflammatory therapy, several other, more selective PDE4 inhibitors have been developed and investigated in a clinical setting. The clinical development of many of the first-generation PDE4 inhibitors such as rolipram was discontinued due to dose-limiting side effects, primarily nausea and emesis. Second-generation PDE4 inhibitors with apparently less pronounced adverse effects are currently in clinical trials (Houslay, supra). PDE-4 inhibitors are for example disclosed in EP 0771794 and EP 0943613.

There is a continued need for developing novel PDE4 inhibitors which have a more favourable therapeutic window, i.e. fewer adverse effects, while retaining their therapeutic anti-inflammatory effect.

SUMMARY OF THE INVENTION

The inventors have surprisingly found that novel compounds of the present invention exhibit PDE4 inhibitory activity and may be useful as therapeutic agents for inflammatory allergic diseases such as bronchial asthma, allergic rhinitis, and nephritis; autoimmune diseases such as rheumatoid arthritis, multiple sclerosis, Crohn's disease, and systemic lupus erythematosus; diseases of the central nervous system such as depression, amnesia, and dementia; organopathy associated with ischemic reflux caused by cardiac failure, shock, and cerebrovascular diseases, and the like; insulin-resistant diabetes; wounds; AIDS, and the like.

Compounds of the present invention may also be beneficial in preventing, treating or ameliorating a variety of diseases, such as dermal diseases or conditions, such as proliferative and inflammatory skin disorders and in particular psoriasis, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Accordingly, the present invention relates to a compound according to formula I,

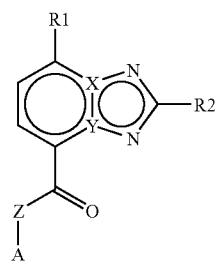

wherein $R_1$ is halogen,
or $R_1$ is alkyl, alkenyl, alkynyl, haloalkyl, alkoxy, cycloalkyl, alkoxycarbonyl, aryl, each being optionally substituted with one or more substituents selected from $R_3$;
$R_2$ is hydrogen,
or $R_2$ is alkyl, cycloalkyl, alkoxy, heterocycloalkyl, aryl, heteroaryl, alkoxycarbonyl, aminocarbonyl, amino,
each being optionally substituted with one or more substituents selected from $R_4$;
$R_3$ is hydrogen, aryl, heteroaryl, oxo, halogen, hydroxy, alkyl, cycloalkyl, alkoxy, or amino;
$R_4$ is hydrogen, halogen, oxo, hydroxy, alkyl, alkoxy, amino, —$NR_aR_b$ or —$C(O)$—$NR_aR_b$, wherein each of $R_a$ and $R_b$ is independently hydrogen, hydroxy, alkyl, alkenyl, aryl, cycloalkyl, heterocycloalkyl, heteroaryl, alkylaryl or alkylheteroaryl, or $R_a$ and $R_b$ together with the nitrogen atom to which they are attached form a heterocycloalkyl ring, each being optionally substituted with one or more substituents selected from $R_3$, or $R_4$ is aryl or heteroaryl substituted with one or more substituents selected from $R_5$;

X and Y are either C and N or N and C, respectively;

Z is $CH_2$, $CH_2$—$CH_2$, $CH_2$—NH, or NH;

A is aryl, cycloalkyl, cycloalkenyl, heteroaryl, heterocycloalkyl or heterocycloalkenyl, each being optionally substituted with one or more substituents selected from the group consisting of $R_5$;

$R_5$ is hydrogen, halogen, oxo, alkyl or alkoxy;

and pharmaceutically acceptable salts, hydrates, N-oxides or solvates thereof.

In another aspect, the invention relates to a compound of general structure I as defined herein for use in therapy, such as for the use in the treatment of dermal diseases or conditions or acute or chronic cutaneous wound disorders.

In another aspect, the invention relates to a pharmaceutical composition comprising a compound of general formula I as defined above together with a pharmaceutically acceptable vehicle or excipient or pharmaceutically acceptable carrier(s), optionally together with one or more other therapeutically active compound(s).

In yet another aspect, the invention relates to the use of a compound of general formula I as defined above, and pharmaceutically acceptable and physiologically cleavable esters, pharmaceutically acceptable salts, hydrates, N-oxides or solvates thereof, in the manufacture of a medicament for the prophylaxis, treatment or amelioration of dermal diseases or conditions, or acute or chronic cutaneous wound disorders.

In yet another aspect, the invention relates to a method of preventing, treating or ameliorating dermal diseases or conditions, or acute or chronic cutaneous wound disorders, the method comprising administering to a person suffering from at least one of said diseases an effective amount of one or more compounds of formula I as defined above and pharmaceutically acceptable and physiologically cleavable esters, pharmaceutically acceptable salts, hydrates, N-oxides or solvates thereof;

optionally together with a pharmaceutically acceptable carrier or one or more excipients, optionally in combination with other therapeutically active compounds.

DETAILED DESCRIPTION OF THE INVENTION

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-20 carbon atoms, and preferably comprises 1-12, e.g. 1-6, e.g. 1-4, e.g. 1-3, e.g. 1-2 carbon atoms. The term includes alkyl, alkenyl, cycloalkyl, cycloalkenyl, alkynyl and aryl, as indicated below.

The term "aryl" is intended to indicate a radical of aromatic carbocyclic rings comprising 6-20 carbon atoms, such as 6-14 carbon atoms, preferably 6-10 carbon atoms, in particular 5- or 6-membered rings, optionally fused carbocyclic rings with at least one aromatic ring, such as phenyl, naphthyl, indenyl and indanyl.

The term "heteroaryl" is intended to indicate radicals of heterocyclic aromatic rings comprising 1-6 heteroatoms (selected from O, S and N) and 1-20 carbon atoms, such as 1-5 heteroatoms and 1-10 carbon atoms, such as 1-5 heteroatoms and 1-6 carbon atoms, such as 1-5 heteroatoms and 1-3 carbon atoms, in particular 5- or 6-membered rings with 1-4 heteroatoms selected from O, S and N, or optionally fused bicyclic rings with 1-4 heteroatoms, and wherein at least one ring is aromatic, e.g. pyridyl, quinolyl, isoquinolyl, indolyl, tetrazolyl, thiazolyl, imidazolyl, pyrazolyl, oxazolyl, isoxazolyl, thienyl, pyrazinyl, isothiazolyl, benzimidazolyl and benzofuranyl.

In the present context, the term "alkyl" is intended to indicate the radical obtained when one hydrogen atom is removed from a hydrocarbon. Said alkyl may be branched or straight and may comprise 1-20, preferably 1-12, such as 1-6, such as 1-4 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, pentyl, isopentyl, hexyl and isohexyl.

The term "cycloalkyl" is intended to indicate a saturated cycloalkane radical, including polycyclic radicals, such as bicyclic or tricyclic radicals, comprising 3-20 carbon atoms, preferably 3-10 carbon atoms, in particular 3-8 carbon atoms, such as 3-6 carbon atoms, such as 4-5 carbon atoms, e.g. cyclopropyl, cyclobutyl, cyclopentyl, cyclohexyl, cycloheptyl, cyclooctyl, bicyclo[2.2.1]heptyl and adamantyl.

The term "cycloalkenyl" is intended to indicate mono-, di-, tri- or tetraunsaturated non-aromatic cyclic hydrocarbon radicals, including polycyclic radicals, comprising 3-20 carbon atoms, typically comprising 3-10 carbon atoms, such as 3-6 carbon atoms, such as 4-5-carbon atoms, e.g. cyclopropenyl, cyclobutenyl, cyclopentenyl, cyclohexenyl, bicyclo[2.2.1]heptenyl, or bicyclo[4.1.0]heptenyl.

The term "heterocycloalkyl" is intended to indicate a cycloalkane radical as defined above, comprising 1-6 heteroatoms, preferably 1, 2, or 3 heteroatoms, selected from O, N, or S, e.g. piperidine, [1,3]dioxolane and [1,3]dioxole.

The term "heterocycloalkenyl" is intended to indicate a cycloalkenyl radical as defined above, including polycyclic radicals, optionally fused with carbocyclic rings, comprising 1-6 heteroatoms, preferably 1-3 heteroatoms, selected from O, N, or S, e.g. 1,6-dihydropyridinyl, 2,3-dihydrobenzofuranyl, 4,5-dihydro-1H-[1,2,4]-triazolyl, 4,5-dihydro-oxazolyl, 1H-indazolyl, 1-H-pyrazolyl, or 4,5-dihydro-isoxazolyl.

The term "alkenyl" is intended to indicate a mono-, di-, tri-, tetra- or pentaunsaturated hydrocarbon radical comprising 2-10 carbon atoms, in particular 2-6 carbon atoms, such as 2-4 carbon atoms, e.g. ethenyl, propenyl, butenyl, pentenyl or hexenyl.

The term "alkynyl" is intended to indicate an hydrocarbon radical comprising 1-5 C-C triple bonds and 2-20 carbon atoms, the alkane chain typically comprising 2-10 carbon atoms, in particular 2-6 carbon atoms, such as 2-4 carbon atoms, e.g. ethynyl, propynyl, butynyl, pentynyl or hexynyl.

The term "halogen" is intended to indicate a substituent from the $7^{th}$ main group of the periodic table, such as fluoro, chloro, bromo and iodo.

The term "haloalkyl" is intended to indicate an alkyl group as defined above substituted with one or more halogen atoms as defined above, e.g. fluoro.

The term "alkoxy" is intended to indicate a radical of the formula —OR', wherein R' is alkyl as indicated above, e.g. methoxy, ethoxy, n-propoxy, isopropoxy, butoxy, etc.

The term "amino" is intended to indicate a radical of the formula —$NR_2$, wherein each R independently represents hydrogen, alkyl, alkenyl, cycloalkyl, or aryl as indicate above, e.g. —$NH_2$, aminophenyl, methylamino, diethylamino, cyclohexylamino, —NH-phenyl, tert-butylamino or ethylamino.

The term "alkoxycarbonyl" is intended to indicate a radical of the formula —C(O)—O—R', wherein R' is alkyl as indicated above, e.g. methoxycarbonyl, ethoxycarbonyl, n-propoxycarbonyl, isopropoxycarbonyl, etc.

The term "alkylaryl" is intended to indicate a radical of the formula —R'—Ar, wherein R' is alkyl as defined above and Ar is aryl as defined above.

The term "alkylheteroaryl" is intended to indicate a radical of the formula —R'-Het, wherein R' is alkyl as defined above and Het is heteroaryl as defined above.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, silver hydroxide, ammonia or the like, or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylenediamine, and dibenzylamine, or L-arginine or L-lysine. Salts obtained by reaction with a suitable base include, but are not limited to sodium salts, choline salts, 2-(dimethylamino)-ethanol salts, 4-(2-hydroxyethyl)-morpholin salts, L-lysine salts, N-(2-hydroxyethyl)-pyrrolidine salts, ethanolamine salts, potassium salts, tetrabutylammonium salts, benzyltrimethylammonium salts, cetyltrimethylammonium salts, tetramethylammonium salts, tetrapropylammonium salts, tris(hydroxymethyl)aminomethane salts, N-methyl-D-glucamine salts, silver salts, benzethonium salts, and triethanolamine salts.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

EMBODIMENTS OF THE PRESENT INVENTION

In one or more embodiments of the present invention A is optionally substituted heteroaryl.

In one or more embodiments of the present invention A is optionally substituted pyridyl.

In one or more embodiments of the present invention A is substituted with one or more substituents selected from chlorine, fluorine, or bromine.

In one or more embodiments of the present invention A is 4-(3,5-dichloropyridyl).

In one or more embodiments of the present invention $R_1$ is $C_{1-6}$ alkoxy or halogen.

In one or more embodiments of the present invention $R_1$ is methoxy.

In one or more embodiments of the present invention the compound of general formula I is a compound of general formula Ia

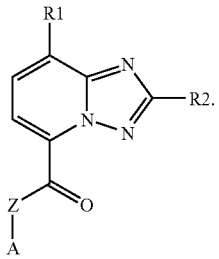

In one or more embodiments of the present invention Z is $CH_2$.

In one or more embodiments of the present invention $R_2$ is optionally substituted $C_{1-6}$ alkyl or optionally substituted $C_{1-6}$ cycloalkyl.

In one or more embodiments of the present invention $R_2$ is cyclopropyl.

In one or more embodiments of the invention, $R_4$ is —C(O)—$NR_aR_b$, wherein $R_a$ and $R_b$ are both hydrogen, or one of $R_a$ and $R_b$ is hydrogen and the other is hydroxy, alkyl, alkenyl, aryl, cycloalkyl, heterocycloalkyl, heteroaryl, alkylaryl or alkylheteroaryl, or $R_a$ and $R_b$ together with the nitrogen atom to which they are attached form a heterocycloalkyl ring.

Examples of compounds of formula I may be selected from the group consisting of 1-(2-cyclopropyl-8-methoxy-[1,2,4]triazolo[1,5-a]pyridin-5-yl)-2-(3,5-dichloro-pyridin-4-yl)-ethanone (compound 101), 2-(3,5-Dichloro-pyridin-4-yl)-1-(8-methoxy-[1,2,4]triazolo[1,5-a]pyridin-5-yl)-ethanone (compound 102), 2-(3,5-Dichloro-pyridin-4-yl)-1-(2-furan-2-yl-8-methoxy-[1,2,4]triazolo[1,5-a]pyridin-5-yl)-ethanone (compound 103), 1-(2-Benzyloxymethyl-8-methoxy-[1,2,4]triazolo[1,5-a]pyridin-5-yl)-2-(3,5-dichloro-pyridin-4-yl)-ethanone (compound 104), 2-(3,5-Dichloro-pyridin-4-yl)-1-(2-hydroxymethyl-8-methoxy-[1,2,4]triazolo[1,5-a]pyridin-5-yl)-ethanone (compound 105), 2-(3,5-Dichloro-pyridin-4-yl)-1-[2-(1-hydroxymethyl-cyclopropyl)-8-methoxy-[1,2,4]triazolo[1,5-a]pyridin-5-yl]-ethanone (compound 106), 2-(3,5-Dichloro-pyridin-4-yl)-1-(8-methoxy-2-methyl-[1,2,4]triazolo[1,5-a]pyridin-5-yl)-ethanone (compound 107), 1-{5-[2-(3,5-Dichloro-pyridin-4-yl)-acetyl]-8-methoxy-[1,2,4]triazolo[1,5-a]pyridin-2-yl}-cyclopropanecarboxylic acid (compound 108), 2-(3,5-Dichloro-pyridin-4-yl)-1-{8-methoxy-2-[1-(morpholine-4-carbonyl)-cyclopropyl]-[1,2,4]triazolo[1,5-a]pyridin-5-yl}-ethanone (compound 109), 1-{5-[2-(3,5-Dichloro-pyridin-4-yl)-acetyl]-8-methoxy-[1,2,4]triazolo[1,5-a]pyridin-2-yl}-cyclopropanecarboxylic acid benzylamide (compound 110), 1-{5-[2-(3,5-Dichloro-pyridin-4-yl)-acetyl]-8-methoxy-[1,2,4]triazolo[1,5-a]pyridin-2-yl}-cyclopropanecarboxylic acid propylamide (compound 111), 1-{5-[2-(3,5-Dichloro-pyridin-4-yl)-acetyl]-8-methoxy-[1,2,4]triazolo[1,5-a]pyridin-2-yl}-cyclopropanecarboxylic acid (pyridin-2-ylmethyl)-amide (compound 112), 1-{5-[2-(3,5-Dichloro-pyridin-4-yl)-acetyl]-8-methoxy-[1,2,4]triazolo[1,5-a]pyridin-2-yl}-cyclopropanecarboxylic acid (pyridin-3-ylmethyl)-amide (compound 113), 1-{5-[2-(3,5-Dichloro-pyridin-4-yl)-acetyl]-8-methoxy-[1,2,4]triazolo[1,5-a]pyridin-2-yl}-cyclopropanecarboxylic acid (pyridin-4-ylmethyl)-amide (compound 114), 1-{5-[2-(3,5-Dichloro-pyridin-4-yl)-acetyl]-8-methoxy-[1,2,4]triazolo[1,5-a]pyridin-2-yl}-cyclopropanecarboxylic acid (2,2-dimethyl-propyl)-amide (compound 115), 1-{5-[2-(3,5-Dichloro-pyridin-4-yl)-acetyl]-8-methoxy-[1,2,4]triazolo[1,5-a]pyridin-2-yl}-cyclopropanecarboxylic acid cyclopentylamide (compound 116), 1-{5-[2-(3,5-Dichloro-pyridin-4-yl)-acetyl]-8-methoxy-[1,2,4]triazolo[1,5-a]pyridin-2-yl}-cyclopropanecarboxylic acid isopropylamide (compound 117), 1-{5-[2-(3,5-Dichloro-pyridin-4-yl)-acetyl]-8-methoxy-[1,2,4]triazolo[1,5-a]pyridin-2-yl}-cyclopropanecarboxylic acid amide (compound 118), 1-{2-[1-(Benzylamino-methyl)-cyclopropyl]-8-methoxy-[1,2,4]triazolo[1,5-a]pyridin-5-yl}-2-(3,5-dichloro-pyridin-4-yl)-ethanone (compound 119), 1-[2-(1-Hydroxymethyl-cyclopropyl)-8-methoxy-[1,2,4]triazolo[1,5-a]pyridin-5-yl]-2-pyrazin-2-yl-ethanone (compound 120), 1-[2-(1-Hydroxymethyl-cyclopropyl)-8-methoxy-[1,2,4]triazolo[1,5-a]pyridin-5-yl]-2-quinolin-4-yl-ethanone (compound 121), 1-[2-(1-Hydroxymethyl-cyclopropyl)-8-methoxy-[1,2,4]triazolo[1,5-a]pyridin-5-yl]-2-pyridin-4-yl-ethanone (compound 122), 2-(3,5-Dibromo-pyridin-4-yl)-1-[2-(1-hydroxymethyl-cyclopropyl)-8-methoxy-[1,2,4]triazolo[1,5-a]pyridin-5-yl]-ethanone (compound 123), 2-(3-Bromo-pyridin-4-yl)-1-[2-(1-hydroxymethyl-cyclopropyl)-8-methoxy-[1,2,4]triazolo[1,5-a]pyridin-5-yl]-ethanone (compound 124), 4-{2-[2-(1-Hydroxymethyl-cyclopropyl)-8-methoxy-[1,2,4]triazolo[1,5-a]pyridin-5-yl]-2-oxo-ethyl}-pyridine-2-carbonitrile (compound 125), 2-(3-Chloro-pyrazin-2-yl)-1-[2-(1-hydroxymethyl-cyclopropyl)-8-methoxy-[1,2,4]triazolo[1,5-a]pyridin-5-yl]-ethanone (compound 126), 2-(2-Chloro-phenyl)-1-(2-cyclopropyl-8-methoxy-[1,2,4]triazolo[1,5-a]pyridin-5-yl)-ethanone (compound 127), 1-(2-Cyclopropyl-8-methoxy-[1,2,4]triazolo[1,5-a]pyridin-5-yl)-2-(3,5-dichloro-1-oxy-pyridin-4-yl)-ethanone (compound 128), and pharmaceutically acceptable salts, hydrates, N-oxides or solvates thereof.

In one or more embodiments of the present invention, the compounds of general formula I have a molecular weight below 800 Dalton, such as below 750 Dalton, e.g. below 700 Dalton, or below 650, 600, 550, or 500 Dalton.

In one or more embodiments of the present invention, the compounds of formula I as defined above are useful in therapy, such as for the use in the treatment of dermal diseases or conditions or acute or chronic cutaneous wound disorders.

In one or more embodiments of the present invention, the dermal disease or condition is selected from the group consisting of proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Compounds of formula I may or may not comprise asymmetrically substituted (chiral) carbon atoms which give rise to the existence of isomeric forms, e.g. enantiomers and possibly diastereomers. The present invention relates to all such isomers, either in pure form or as mixtures thereof (e.g. racemates). Pure stereoisomeric forms of the compounds and the intermediates of this invention may be obtained by the application of procedures known in the art. The various isomeric forms may be separated by physical separation methods such as selective crystallization and chromatographic techniques, e.g. liquid chromatography using chiral stationary phases. Enantiomers may be separated from each other by the selective crystallization of their diastereomeric salts with optically active amines, such as I-ephedrine. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably, if a specific stereoisomer is desired, said compound will be synthesized by stereoselective or stereospecific methods of preparation. These methods will advantageously employ chiral pure starting materials.

Compounds of the invention, optionally in combination with other active compounds, may be useful for the treatment of dermal diseases or conditions, or acute or chronic cutaneous wound disorders, in particular for the treatment of proliferative and inflammatory skin disorders, psoriasis, cancer, epidermal inflammation, alopecia, skin atrophy, steroid induced skin atrophy, skin ageing, photo skin ageing, acne, dermatitis, atopic dermatitis, seborrheic dermatitis, contact dermatitis, urticaria, pruritis, and eczema.

Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition. The invention therefore relates to a pharmaceutical composition comprising a compound of formula I, optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

Conveniently, the active ingredient comprises from 0.05-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.1 mg and 1000 mg, preferably between 1 mg and 100 mg, such as 5-50 mg of a compound of formula I.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 400 mg/kg body weight. The compound may be administered as a bolus (i.e. the entire daily doses is administered at once) or in divided doses two or more times a day.

In the context of topical treatment it may be more appropriate to refer to a "usage unit", which denotes a single dose which is capable of being administered to a patient, and which may be readily handled and packed, remaining as a physically and chemically stable unit dose comprising either the active material as such or a mixture of it with solid or liquid pharmaceutical diluents or carriers.

The term "usage unit" in connection with topical use means a unitary, i.e. a single dose capable of being administered topically to a patient in an application per square centimeter of the infected area of from 0.1 mg to 10 mg and preferably from 0.2 mg to 1 mg of the active ingredient in question.

It is also envisaged that in certain treatment regimes, administration with longer intervals, e.g. every other day, every week, or even with longer intervals may be beneficial.

If the treatment involves administration of another therapeutically active compound it is recommended to consult *Goodman & Gilman's The Pharmacological Basis of Therapeutics*, 9$^{th}$ Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral (including sustained or timed release), rectal, parenteral (including subcutaneous, intraperitoneal, intramuscular, intraarticular and intravenous), transdermal, ophthalmic, topical, dermal, nasal or buccal administration. Topical administration of the claimed formulation is particularly suitable.

The formulations may conveniently be presented in dosage unit form and may be prepared by any of the methods well known in the art of pharmacy, e.g. as disclosed in Remington, *The Science and Practice of Pharmacy*, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops. Compositions for ophthalmic treatment may preferably additionally contain a cyclodextrin.

For topical administration, the compound of formula I may typically be present in an amount of from 0.01 to 20% by weight of the composition, such as 0.1% to about 10%, but may also be present in an amount of up to about 50% of the composition.

Formulations suitable for nasal or buccal administration include powder, self-propelling and spray formulations, such as aerosols and atomisers. Such formulations are disclosed in greater detail in e.g. Modern Pharmaceutics, 2$^{nd}$ ed., G. S. Banker and C. T. Rhodes (Eds.), page 427-432, Marcel Dekker, New York; Modern Pharmaceutics, 3$^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

The pharmaceutical composition may additionally comprise one or more other active components conventionally used in the treatment of dermal disease or conditions, e.g. selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, salicylates, indomethacin, flufenamate, naproxen, timegadine, gold salts, penicillamine, serum cholesterol lowering agents, retinoids, zinc salts, salicylazosulfapyridine and calcineurin inhibitors.

The term "compound of formula I" as used herein is intended to include compounds of formula Ia.

Methods of Preparation

The compounds of the present invention can be prepared in a number of ways well known to those skilled in the art of synthesis. The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art of organic synthesis. Not all compounds falling into a given class may be compatible with some of the reaction conditions required in some of the methods described. Such restrictions to the substituents which are compatible with the reaction conditions will be readily apparent to one skilled in the art and alternative methods can be used.

Starting materials are either known or commercially available compounds or can be prepared by routine synthetic methods well known to a person skilled in the art.

General Procedures, Preparations and Examples $^1$H nuclear magnetic resonance (NMR) spectra were recorded at 300 MHz and $^{13}$C NMR spectra at 75.6 MHz or 151 MHz. Chemical shift values (δ, in ppm) are quoted in the specified solvent relative to internal tetramethylsilane (δ=0.00) or chloroform (δ=7.25) or deuteriochloroform (δ=76.81 for $^{13}$C NMR) standards. The value of a multiplet, either defined (doublet (d), triplet (t), quartet (q)) or not (m) at the approximate mid point is given unless a range is quoted. (bs) indicates a broad singlet. The organic solvents used were usually anhydrous. Chromatography was performed on Merck silica gel 60 (0.040-0.063 mm). The solvent ratios indicated refer to v:v unless otherwise noted.

The following abbreviations have been used throughout:
DCM dichloromethane
DMF N,N'-Dimethylformamide
DMSO dimethyl sulfoxide
Et ethyl
L liter
LDA lithium diisopropylamide
LiHMDS lithium Hexamethyldisilazide
m milli
Me methyl
NMR nuclear magnetic resonance
THF tetrahydrofuran
v volume Preparative HPLC/MS Preparative HPLC/MS was performed on a Dionex APS-system with two. Shimadzu PP150 prep. pumps and a Thermo MSQ Plus mass spectrometer. Column: Waters XTerra C-18, 150 mm×19 mm, 5 μm; solventsystem: A water (0.1% formic acid) and B=acetonitrile (0.1% formic acid); flow rate=18 mL/min; method (10 min): Linear gradient method going from 10% B to 100% B in 6 minutes and staying at 100% B for another 2 minutes. The fractions were collected based on ion traces of relevant ions and PDA signal (240-400 nm).

Analytical HPLC/MS

Analytical HPLC/MS was performed on a system consisting of a Waters 2795 HPLC, Micromass ZQ mass spectrometer, Waters 996 PDA. Column: Waters XTerra C-18, 50 mm×3.0 mm, 5 μm; solventsystem: A=water:acetonitrile 95:5 (0.05% formic acid) and B=acetonitrile (0.05% formic acid); flow rate=1.0 mL/min; method (8 min): Linear gradient method going from 10% B to 100% B in 6.0 minutes and staying at 100% B for 1 minute.

General Procedure of Preparation:

The compounds of the invention can for example be prepared by the following general methods:

a) Reaction of compounds of general formula II

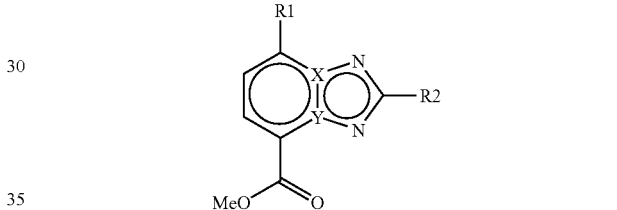

wherein R1, R2, X and Y is defined as described herein, with lithio or magnesio carbanions generated from A-Methyl, wherein A is defined as described herein, and a suitable base, such as LDA or LiHMDS in a suitable solvent such as THF at temperatures from e.g. minus 78° C. to rt.

b) Reaction of compounds of formula II with standard conditions for ester hydrolysis, such as LiOH in a mixture of THF and water followed by treatment of the generated carboxylic acid with (COCl)$_2$, SOCl$_2$ or PCl$_5$ in a suitable solvent such as DCM or toluene with or without catalytic amount of DMF at temperatures from 0° C. to 70° C. to afford the corresponding acid chloride. After evaporation of the solvent in vacuo subsequent condensation of the generated acid chloride with nitrogen-anions, generated by addition a suitable base, such as NaH, LDA or LiHMDS in a suitable solvent, such as THF at temperatures from minus 78° C. to rt to A-NH$_2$, wherein A is defined as described herein, are performed.

Starting materials of formula II are prepared according to standard procedures known to a chemist skilled in the art of organic synthesis. Compounds, wherein X is C and Y is N, are for example prepared by O-alkylation of commercially available 6-methyl-2-nitro-pyridin-3-ol with alkyl iodides in the presence of a suitable base, such as K$_2$CO$_3$ or Et$_3$N, in a suitable solvent, such as DMF, THF or DCM at temperatures from rt to 100° C., followed by oxidation of the 6-methyl group by a suitable oxidant such as KMnO$_4$ in a suitable solvent such as water at temperatures from rt to 100° C. The resulting carboxylic acid is esterified with MeI in the presence of a suitable base, such as K$_2$CO$_3$ or Et$_3$N in a suitable solvent such as DMF, THF or DCM at temperatures from rt to 100° C. (all three steps are according to well-known literature procedures, e.g. *Tet. Lett.* (1995), 36, 5319-22). The nitro group is then reduced by a suitable reductant such as SnCl₂ in DMF or Fe under acidic conditions in a suitable solvent such as AcOH at temperatures from rt to 100° C. (*J. Org. Chem.* (2000), 65, 2847-50). The resulting 2-amino pyridines are N-aminated at the pyridine nitrogen using O-mesitylensulfonyl hydroxylamine and then treated with aldehydes to form the desired 1,2,4-trizolo-[1,5,a]-pyridine heterocycles according to known procedures (*Tet. Lett.* (2003), 44, 1675-78).

EXAMPLES

Preparation 1

Compound 201

3-Methoxy-6-methyl-2-nitro-pyridine

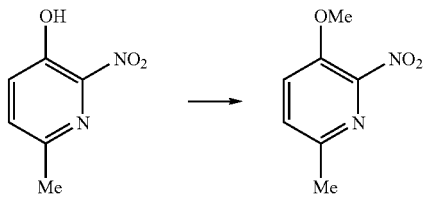 [SMILES: Cc1ccc(O)c([N+](=O)[O-])n1 ; COc1ccc(C)nc1[N+](=O)[O-]]

Commercially available 6-Methyl-2-nitro-pyridin-3-ol (Aldrich) (5.09 g, 33 mmol) in acetone (50 mL) was treated with K₂CO₃ (5.47 g, 39.6 mmol) and MeI (3.09 mL, 49.5 mmol). The orange suspension was heated to 50° C. for 90 hours. After evaporation of the solvent in vacuo the crude mixture was treated with 1N NaOH (50 mL) and extracted with EtOAc (2×50 mL) the combined organic phases was washed with brine (2×50 mL), dried over Na₂SO₄, filtered and concentrated in vacuo. 3-Methoxy-6-methyl-2-nitro-pyridine was obtained as a yellow solid.

¹H NMR (CDCl₃) δ=7.42 (1H, d), 7.36 (1H, d), 3.94 (3H, s), 2.53 (3H, s).

LC/MS: (m/z) 169.2 (MH+); RT=2.35 min; purity (UV)=100%

Preparation 2

Compound 202

Methoxy-6-nitro-pyridine-2-carboxylic acid

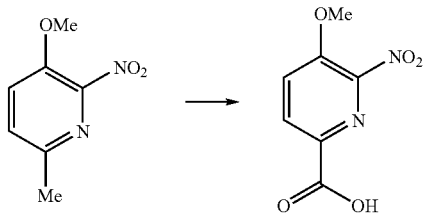 [SMILES: COc1ccc(C)nc1[N+](=O)[O-] ; COc1ccc(C(=O)O)nc1[N+](=O)[O-]]

To KMnO₄ (31.2 g, 62.2 mmol) dissolved in water (400 mL) was added 3-methoxy-6-methyl-2-nitro-pyridine obtained in preparation 1. The mixture was heated to 75° C. for 18 hours. The hot reaction mixture was filtered through celite and the celite was washed with additional water (200 mL). The reaction mixture was cooled on ice and treated portion wise with 2N HCl (70 mL) and brine (100 mL). The product was extracted with EtOAc (3×200 mL) the combined organic phases were dried over Na₂SO₄, filtered and concentrated in vacuo. 5-Methoxy-6-nitro-pyridine-2-carboxylic acid was obtained as a slightly yellow solid.

¹H NMR (CD₃OD) δ=8.37 (1H, d), 7.93 (1H, d), 4.06 (3H, s).

LC/MS: (m/z) 199.1 (MH+); RT=1.80 min; purity (UV)=100%

Preparation 3

Compound 203

Methoxy-6-nitro-pyridine-2-carboxylic acid methyl ester

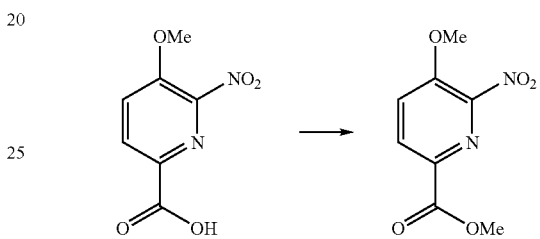

5-Methoxy-6-nitro-pyridine-2-carboxylic acid obtained in preparation 2 (2.54 g, 12.8 mmol) in DMF (25 mL) was treated with K₂CO₃ (2.2 g, 15.9 mmol) and MeI (1.2 mL, 19.2 mmol). The orange suspension was heated to 50° C. for 48 hours. After evaporation of the solvent in vacuo the crude mixture was treated with water (50 mL) and extracted with EtOAc (2×50 mL) the combined organic phases were washed with brine (2×50 mL), dried over Na₂SO₄, filtered and concentrated in vacuo to provide 2.75 g crude. The product was purified by flash chromatography on silica using EtOAc in heptane as eluent. 5-Methoxy-6-nitro-pyridine-2-carboxylic acid methyl ester was obtained as a slightly yellow solid.

¹H NMR (CDCl₃) δ=8.36 (1H, d), 7.59 (1H, d), 4.05 (3H, s), 4.00 (3H, s).

Preparation 4

Compound 204

6-Amino-5-methoxy-pyridine-2-carboxylic acid methyl ester

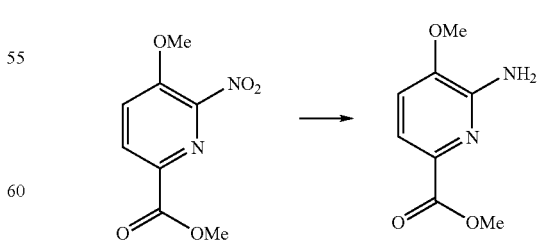

5-Methoxy-6-nitro-pyridine-2-carboxylic acid methyl ester obtained in preparation 3 (1.11 g, 5.25 mmol) and Fe (1.76 g, 31.5 mmol) were mixed in acetic acid (20 mL). The reaction reaction mixture was heated to 100° C. for 30 min.

After cooling of the yellow reaction mixture to rt the solvent was removed in vacuo and then added to NaHCO$_3$ (sat., 100 mL). The product was extracted with EtOAc (5×60 mL) and the combined organic phases were dried over Na$_2$SO$_4$, filtered and concentrated in vacuo. 6-Amino-5-methoxy-pyridine-2-carboxylic acid methyl ester was obtained as a white solid.

$^1$H NMR (DMSO-d$_6$) δ=7.33 (1H, d), 7.09 (1H, d), 6.07 (2H, s), 3.84 (3H, s), 3.77 (3H, s).

$^{13}$C NMR (DMSO-d$_6$) δ=165.8, 150.8, 145.7, 136.6, 115.7, 114.6, 55.9, 51.9.

Preparation 5

Compound 205

2-Cyclopropyl-8-methoxy-[1,2,4]triazolo[1,5-a]pyridine-5-carboxylic acid methyl ester

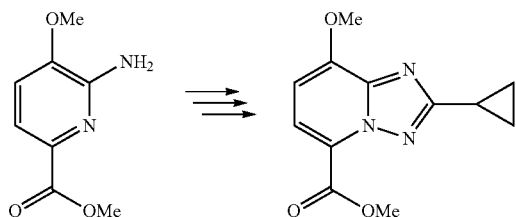 [SMILES: COC(=O)c1ccc(OC)c(N)n1 ; COC(=O)c1ccc(OC)c2nc(C3CC3)nn12]

Ethyl O-mesitylsulfonylacetohydroxamate (180 mg, 0.63 mmol) and dioxane (120 µL) were mixed under Argon. The suspension was cooled on ice and treated with 70% HClO$_4$ (72 µL). After 15 min. at 0° C. ice-cooled water (2 mL) was added and the white precipitate was filtered and washed with additional ice-cooled water. The precipitate was re-dissolved in DCM (2 mL), see *J. Org. Chem.* (1973), 38, 1239. The solution was added to 6-amino-5-methoxy-pyridine-2-carboxylic acid methyl ester obtained in preparation 4 (100 mg, 0.549 mmol) in DCM (1 mL). The slightly yellow solution was stirred at rt for 90 minutes and then treated with tert-butyl methyl ether (1.5 mL). The white precipitate formed was filtered to provide 151 mg of a white solid, which was re-dissolved in dioxane (5 mL) and treated with cyclopropane carboxaldehyde (36.9 µL) and heated to 90° C. for 3 hours. The reaction mixture was cooled to rt and treated with 1N KOH (380 µL) in MeOH (2 mL) and left at rt for 17 hours. The solvent was evaporated in vacuo and then added to NaHCO$_3$ (sat., 4 mL). The product was extracted with EtOAc (2×10 mL) and the combined organic phases were dried over Na$_2$SO$_4$, filtered and concentrated in vacuo. The product was purified by flash chromatography on silica using EtOAc in heptane as eluent. 2-Cyclopropyl-8-methoxy-[1,2,4]triazolo[1,5-a]pyridine-5-carboxylic acid methyl ester was obtained as a white solid.

$^1$H NMR (CDCl$_3$) δ=7.70 (1H, d), 6.75 (1H, d), 4.09 (3H, s), 4.02 (3H, s), 2.35 (1H, m), 1.22 (2H, m), 1.07 (2H, m).

LC/MS: (m/z) 248.2 (MH+); RT=2.12 min; purity (UV)=100%

The procedure described in Preparation 5 was used with other carbaldehydes:

Preparation 6

Compound 206

8-Methoxy-[1,2,4]triazolo[1,5-a]pyridine-5-carboxylic acid methyl ester

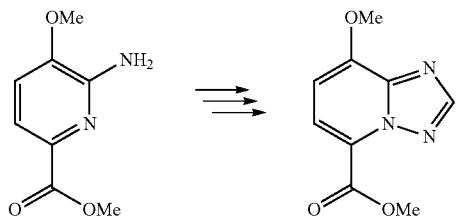 [SMILES: COC(=O)c1ccc(OC)c(N)n1 ; COC(=O)c1ccc(OC)c2ncnn12]

LC/MS: (m/z) 208.2 (MH+); RT=1.62 min; purity (UV)=100%

Aldehyde: Paraformaldehyde

Preparation 7

Compound 207

2-Furan-2-yl-8-methoxy-[1,2,4]triazolo[1,5-a]pyridine-5-carboxylic acid methyl ester

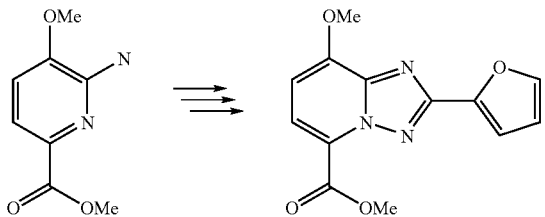 [SMILES: COC(=O)c1ccc(OC)c(N)n1 ; COC(=O)c1ccc(OC)c2nc(-c3ccco3)nn12]

LC/MS: (m/z) 274.2 (MH+); RT=2.37 min; purity (UV)=100%

Aldehyde: Furan-2-ylcarbaldehyde

Preparation 8

Compound 208

2-Benzyloxymethyl-8-methoxy-[1,2,4]triazolo[1,5-a]pyridine-5-carboxylic acid methyl ester

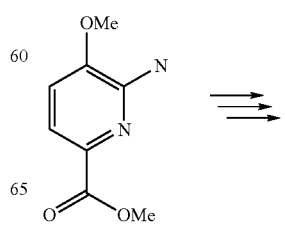

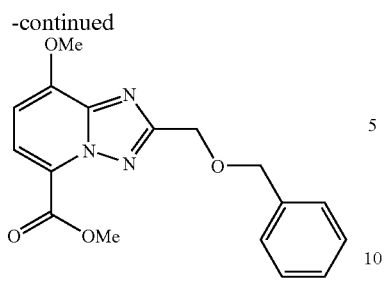

LC/MS: (m/z) 328.3 (MH+); RT=2.96 min; purity (UV)= 100%

Aldehyde: Benzyloxy-acetaldehyde

Preparation 9

Compound 209

8-Methoxy-2-(1-trityloxymethyl-cyclopropyl)-[1,2,4]triazolo[1,5-a]pyridine-5-carboxylic acid methyl ester

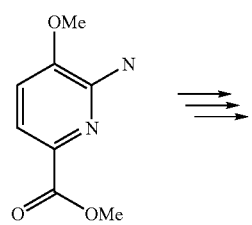

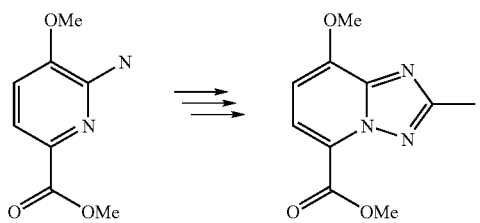 [SMILES: COC(=O)c1ccc(OC)c(N)n1 ; COC(=O)c1ccc(OC)c2nc(C)nn12]

¹H NMR (CDCl₃) δ=7.70 (1H, d), 7.51 (6H, d), 7.26 (9H, m), 6.75 (1H, d), 4.09 (3H, s), 3.97 (3H, s), 3.67, (2H, s), 1.39 (2H, m), 1.05 (2H, m).

Aldehyde: 1-Trityloxymethyl-cyclopropanecarbaldehyde obtained in preparation 13.

Preparation 10

Compound 210

8-Methoxy-2-methyl-[1,2,4]triazolo[1,5-a]pyridine-5-carboxylic acid methyl ester

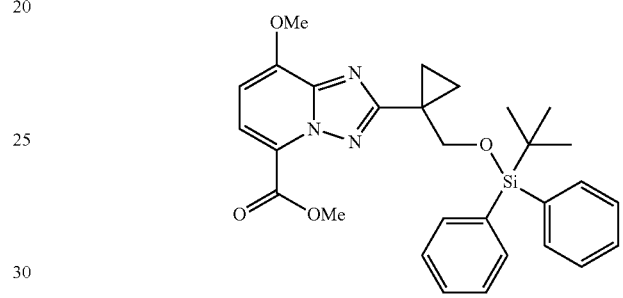

LC/MS: (m/z) 222.3 (MH+); RT=1.67 min; purity (UV)= 100%

Aldehyde: Acetaldehyde

Preparation 11

Compound 211

2-[1-(tert-Butyl-diphenyl-silanyloxymethyl)-cyclopropyl]-8-methoxy-[1,2,4]triazolo[1,5-a]pyridine-5-carboxylic acid methyl ester

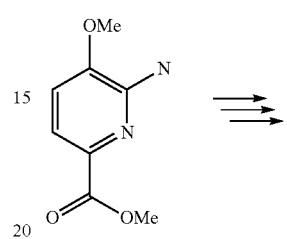

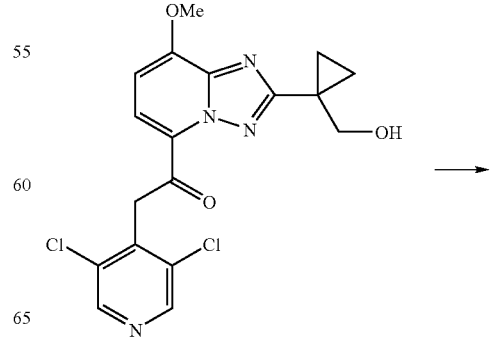

¹H NMR (CDCl₃) δ=7.68 (5H, m), 7.37 (6H, m), 6.73 (1H, d), 4.35, (2H, s), 4.07 (3H, s), 3.96 (3H, s), 1.36 (2H, m), 1.26 (2H, m), 1.02 (9H, s).

LC/MS: (m/z) 516.5 (MH+); RT=5.74 min; purity (UV)= 100%

Aldehyde: 1-(tert-Butyl-diphenyl-silanyloxymethyl)-cyclopropanecarbaldehyde obtained in preparation 14

Preparation 12

Compound 212

1-{5-[2-(3,5-Dichloro-pyridin-4-yl)-acetyl]-8-methoxy-[1,2,4]triazolo[1,5-a]pyridin-2-yl}-cyclopropanecarbaldehyde

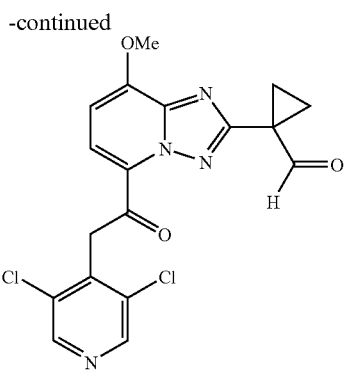

2-(3,5-Dichloro-pyridin-4-yl)-1-[2-(1-hydroxymethyl-cyclopropyl)-8-methoxy-[1,2,4]triazolo[1,5-a]pyridin-5-yl]-ethanone obtained in example 6 (154 mg, 0.38 mmol) was dissolved in DCM (5 mL) and treated with NaHCO$_3$ (127 mg, 1.51 mmol) and Dess-Martin periodinane (321 mg, 0.756 mmol). The suspension was stirred for 30 min at rt and then treated with a 50 mL of a 1:1 mixture of Na$_2$S$_2$O$_3$ (sat., aq.) and NaHCO$_3$ (sat., aq.). The reaction mixture was then extracted with EtOAc (2×25 mL). The combined organic phases were washed with brine and dried over Na$_2$SO$_4$, filtered and concentrated in vacuo. Yield 156 mg of slightly yellow solid, which was used without further purification.

$^1$H NMR (CDCl$_3$) δ=10.59 (1H, s), 8.54 (2H, s), 7.84 (1H, d), 6.94 (1H, d), 5.16 (2H, s), 4.17 (3H, s), 1.89 (4H, m).

LC/MS: (m/z) 405.2 (MH+); RT=3.52 min; purity (UV)=100%

Preparation 13

Compound 213

1-Trityloxy methyl-cyclopropanecarbaldehyde

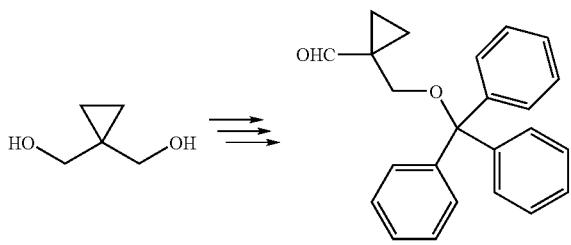 [SMILES: OCC1(CO)CC1 ; O=CC1(COC(c2ccccc2)(c2ccccc2)c2ccccc2)CC1]

1,1-Bis(hydroxymethyl)cyclopropane (1.23 g, 12 mmol) was dissolved in DCM (12 mL) and triethylamine (0.669 mL, 4.8 mmol). Trityl chloride (1.12 g, 4 mmol) was added and the reactionmixture was left at rt for 5 days. The solvent was removed in vacuo. Water (50 mL) was added and the reaction mixture was extracted with EtOAc (2×50 mL). The combined organic phases were washed with brine and dried over Na$_2$SO$_4$, filtered and concentrated in vacuo. Yield 1.47 g of slightly yellow oil, which was used without further purification.

Pyridinium dichromate (1.5 g, 4 mmol) and DCM (6 mL) was mixed and a solution of the crude material obtained above (0.689 g, 2 mmol) dissolved in DCM (2 mL) was added. The suspension was left at room temperature o/n. The reaction mixture was filtered through celite and the solvent removed in vacuo. The crude was redissolved in toluene (10 mL) and the solvent removed in vacuo.

The crude was redissolved in tertbutylmethyl ether (10 mL) filtered through celite and the solvent removed in vacuo to provide 665 mg of an yellow oil. 440 mg of this oil was purified by flash chromatography on silica using EtOAc (8%) in heptane as eluent. Yield 0.295 g of a white solid.

$^1$H NMR (CDCl$_3$) δ=9.15 (1H, s), 7.45-7.23 (15H, m), 7.41 (6H, m), 3.38 (2H, s), 1.20 (2H, m), 1.04 (2H, m).

Preparation 14

Compound 214

1-(tert-Butyl-diphenyl-silanyloxymethyl)-cyclopropanecarbaldehyde

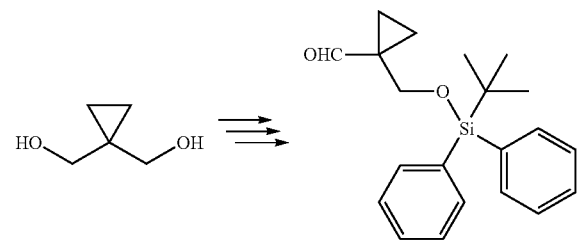 [SMILES: OCC1(CO)CC1 ; CC(C)(C)[Si](OCC1(C=O)CC1)(c1ccccc1)c1ccccc1]

1,1-Bis(hydroxymethyl)cyclopropane (5.44 g, 53.3 mmol) was dissolved in DCM (53 mL) and triethylamine (1.98 mL, 21.4 mmol). Diphenyltertbutylsilyl chloride (4.89 g, 17.8 mmol) was added and the reaction mixture was left at rt for 2.5 hours. The solvent was removed in vacuo. EtOAc (50 mL) was added and the reaction mixture was washed with water (2×50 mL) and brine (50 mL). The organic phase was dried over Na$_2$SO$_4$, filtered and concentrated in vacuo. Yield 6.62 g of slightly yellow oil, which was used without further purification.

Oxalyl chloride (2.04 g, 16.1 mmol) and DCM (36 mL) was cooled to −78° C. and treated with DMSO (2.29 mL) in DCM (3 mL). The colourless solution was stirred for 10 min and then treated dropwise with a solution of the crude obtained above (4.75 g, 14 mmol) dissolved in DCM (10 mL). The white suspension was left for 30 minutes and then treated dropwise with triethyl amine (7.47 mL, 53.6 mmol). The reaction mixture was left for additional 20 minutes and the cooling bath was removed and the reaction mixture was brought to rt and stirred for 20 minutes at rt. The suspension was mixed with water (50 mL) and extracted with DCM (2×50 mL). The combined organic phases were dried over Na$_2$SO$_4$, filtered and concentrated in vacuo to provide 4.9 g of an yellow oil. The product was purified by flash chromatography on silica using EtOAc (0 to 4%) in heptane as eluent. Yield 4.41 g of a colourless oil.

$^1$H NMR (CDCl$_3$) δ=9.11 (1H, s), 7.66 (4H, d), 7.41 (6H, m), 3.95 (2H, s), 1.14 (2H, m), 1.10 (2H, m), 1.04 (9H, s).

General Procedure for Preparation of Compounds of Formula Ib, wherein R2 is as Defined Herein:

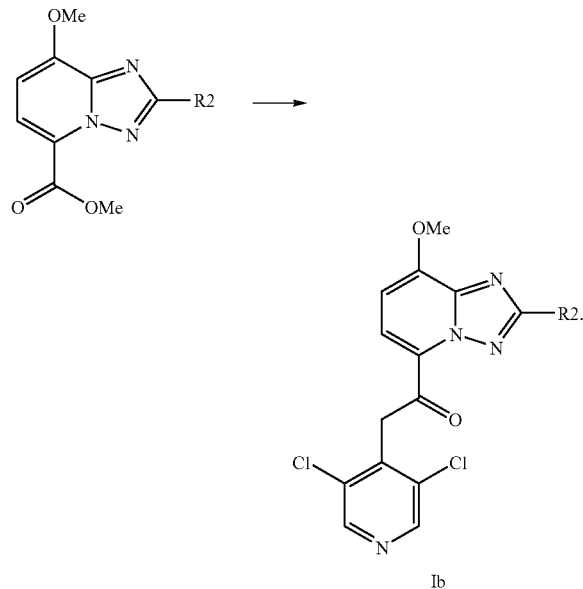

A derivative of 8-methoxy-[1,2,4]triazolo[1,5-a]pyridine-5-carboxylic acid methyl ester from the previously described preparations (0.137 mmol) was mixed with 3,5-dichloro-4-methyl-pyridine (0.164 mmol) in dry THF (1 mL). The reaction mixture was cooled on ice and treated dropwise with lithium bis(trimethylsilyl)amide (0.27 mL of an 1 M solution). After 30 min. the cooling bath was removed and the suspension was left at rt for 18 hours. NH$_4$Cl (sat., 1 mL) was added and the product extracted with EtOAc (2×1 mL). The combined organic phases were dried over Na$_2$SO$_4$, filtered and concentrated in vacuo. The product was purified by flash chromatography on silica using EtOAc in heptane as eluent.

Example 1

Compound 101

1-(2-Cyclopropyl-8-methoxy-[1,2,4]triazolo[1,5-a]pyridin-5-yl)-2-(3,5-dichloro-pyridin-4-yl)-ethanone $^1$H NMR (CDCl$_3$) δ=8.53 (2H, s), 7.75 (1H, d), 6.85 (1H, d), 5.17 (2H, s), 4.12 s), 2.33 (1H, m), 1.21 (2H, m), 1.14 (2H, m)

LC/MS: (m/z) 377.1 (MH+); RT=3.65 min; purity (UV)=100%

Starting material: 2-Cyclopropyl-8-methoxy-1,2,4l-triazolo[1,5-a]pyridine-5-carboxylic acid methyl ester from preparation 5

Example 2

Compound 102

2-(3,5-Dichloro-pyridin-4-yl)-1-(8-methoxy-[1,2,4]triazolo[1,5-a]pyridin-5-yl)-ethanone $^1$H NMR (DMSO-d$_6$) δ=8.70 (2H, s), 8.69 (1H, s), 7.96 (1H, d), 7.27 (1H, d), 5.14 (2H, s), 4.12 (3H, s)

Starting material: 8-Methoxy-[1,2,4]triazolo[1,5-a]pyridine-5-carboxylic acid methyl ester obtained in preparation 6

Example 3

Compound 103

2-(3,5-Dichloro-pyridin-4-yl)-1-(2-furan-2-yl-8-methoxy-[1,2,4]triazolo[1,5-a]pyridin-5-yl)-ethanone $^1$H NMR (DMSO-d$_6$) δ=8.70 (2H, s), 7.95 (2H, m), 7.28 (2H, m), 6.73 (1H, dd), 5.17 (2H, s), 4.13 (3H, s)

Starting material: 2-Furan-2-yl-8-methoxy-[1,2,4]triazolo[1,5-a]pyridine-5-carboxylic acid methyl ester obtained in preparation 7

Example 4

Compound 104

1-(2-Benzyloxymethyl-8-methoxy-[1,2,4]triazolo[1,5-a]pyridin-5-yl)-2-(3,5-dichloro-pyridin-4-yl)-ethanone $^1$H NMR (CDCl$_3$) δ=8.54 (2H, s), 7.86 (1H, d), 7.42 (2H, d), 7.33 (1H, t), 7.27 (2H, d), 6.92 (1H, d), 5.17 (2H, s), 4.92 (2H, s), 4.79 (2H, s), 4.16 (3H, s)

$^{13}$C NMR (CDCl$_3$) δ=186.4, 162.8, 152.6, 147.3, 146.2, 140.6, 137.6, 133.5, 129.6, 128.4, 128.0, 127.8, 119.9, 105.5, 73.2, 65.5, 56.9, 45.5.

Starting material: 2-Benzyloxymethyl-8-methoxy-[1,2,4]triazolo[1,5-a]pyridine-5-carboxylic acid methyl ester obtained in preparation 8

Example 5

Compound 105

2-(3,5-Dichloro-pyridin-4-yl)-1-(2-hydroxymethyl-8-methoxy-[1,2,4]triazolo[1,5-a]pyridin-5-yl)-ethanone $^1$H NMR (CDCl$_3$) δ=8.54 (2H, s), 7.87 (1H, d), 6.95 (1H, d), 5.14 (2H, s), 5.04 (2H, m), 4.17 (3H, s), 2.56 (1H, bs)

$^{13}$C NMR (CDCl$_3$) δ=186.2, 165.0, 152.4, 147.3, 146.2, 140.5, 133.4, 129.6, 119.9, 105.7, 58.9, 56.9, 45.4

Starting material: 2-Benzyloxymethyl-8-methoxy-[1,2,4]triazolo[1,5-a]pyridine-5-carboxylic acid methyl ester obtained in preparation 8

Comment: After using the general procedure to generate compound 104 obtained in example 104 the final compound was obtained by debenzylation using iodotrimethylsilane (25 eq.) in dichloromethane (rt for 16 hr) followed by standard work-up and silica column purification using EtOAc in heptane as eluent.

Example 6

Compound 106

2-(3,5-Dichloro-pyridin-4-yl)-1-[2-(1-hydroxymethyl-cyclopropyl)-8-methoxy-[1,2,4]triazolo[1,5-a]pyridin-5-yl]-ethanone $^{13}$C NMR (DMSO-d$_6$) δ=186.6, 167.6, 151.4, 145.2, 140.8, 132.8, 128.4, 119.1, 106.3, 62.9, 56.7, 44.3, 21.8, 12.9

Starting material: 8-Methoxy-2-(1-trityloxymethyl-cyclopropyl)-[1,2,4]triazolo[1,5-a]pyridine-5-carboxylic acid methyl ester from preparation 9

Comment: After using the general procedure to generate the trityl protected compound, the final compound was obtained by detritylation using trifluoroacetic acid (45 eq.) in dichloromethane (rt for 1 hr) followed by standard work-up and silica column purification using EtOAc in heptane as eluent.

Example 7

Compound 107

2-(3,5-Dichloro-pyridin-4-yl)-1-(8-methoxy-2-methyl-[1,2,4]-triazolo[1,5-a]pyridin-5-yl)-ethanone $^1$H NMR (DMSO-$d_6$) δ=8.69 (2H, s), 7.88 (1H, d), 7.22 (1H, d), 5.10 (2H, s), 4.09 (3H, s), 2.56 (3H, s)

$^{13}$C NMR (DMSO-$d_6$) δ=186.3, 161.9, 151.6, 147.1, 145.4, 140.6, 132.7, 128.4, 119.5, 106.3, 56.9, 44.2, 14.2

Starting material: 8-Methoxy-2-methyl-[1,2,4]triazolo[1,5-a]pyridine-5-carboxylic acid methyl ester obtained in preparation 10

Example 8

Compound 108

1-{5-[2-(3,5-Dichloro-pyridin-4-yl)-acetyl]-8-methoxy-[1,2,4]triazolo[1,5-a]pyridin-2-yl}-cyclopropanecarboxylic acid

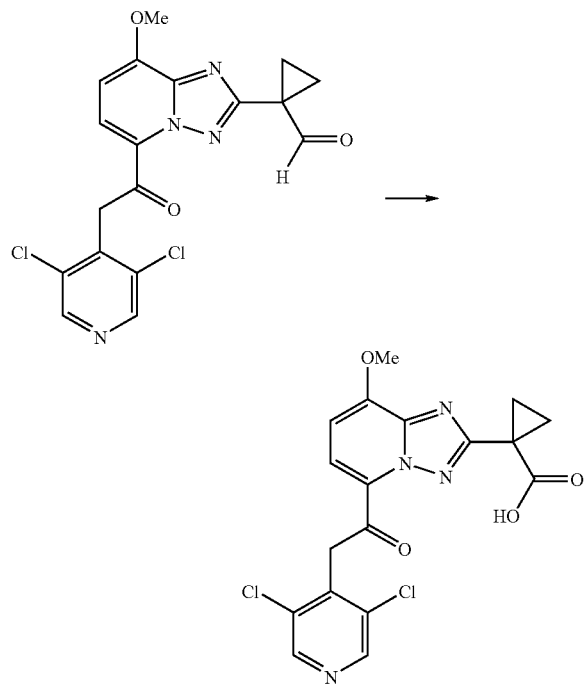

1-{5-[2-(3,5-Dichloro-pyridin-4-yl)-acetyl]-8-methoxy-[1,2,4]triazolo[1,5-a]pyridin-2-yl}-cyclopropanecarbaldehyde from preparation 12 (130 mg, 0.32 mmol), was mixed with tBuOH (20 mL) and water (4 mL). The reaction mixture was treated with sodium dihydrogenphosphate (119 mg, 0.99 mmol), 2-methyl-2-butene (0.187 mL, 1.77 mmol) and sodium chlorite (tech. ~80%, 65 mg, 0.57 mmol). The reaction mixture was left for 2 h at rt and then evaporated to ~5 mL. Brine (15 mL) was added and the mixture was extracted with DCM (3×25 mL). The combined organic phases were dried over $Na_2SO_4$, filtered and concentrated in vacuo to yield 223 mg of a yellow solid. The crude was treated with diethyl ether (2 mL) and filtered to provide 120 mg of a slightly yellow solid.

$^1$H NMR (DMSO-$d_6$) δ=12.75 (1H, bs), 8.69 (2H, s), 7.91 (1H, d), 7.24 (1H, d), 5.10 (2H, s), 4.10 (3H, s), 1.57 (2H, m), 1.50 (2H, m).

$^{13}$C NMR (DMSO-$d_6$) δ=186.2, 173.0, 163.8, 151.7, 147.1, 145.0, 140.6, 132.7, 128.4, 120.1, 106.4, 56.9, 44.1, 23.1, 15.9.

LC/MS: (m/z) 421.2 (MH+); RT=3.08 min; purity (UV)=100%

General Procedure for Preparation of Compounds of Formula Ic, Wherein R is as Defined Herein:

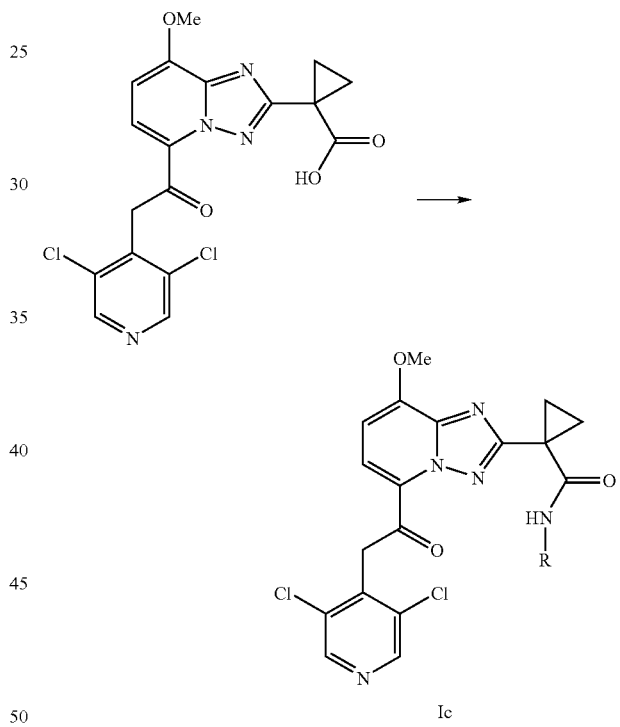

Ic

1-{5-[2-(3,5-Dichloro-pyridin-4-yl)-acetyl]-8-methoxy-[1,2,4]triazolo[1,5-a]pyridin-2-yl}-cyclopropanecarboxylic acid (0.06 mmol) obtained in example 8 was dissolved in dry DMF (0.3 mL). Triethylamine (0.18 mmol) and HATU (0.09 mmol) was added followed by a primary or secondary amine (0.09 mmol). The reaction mixture was left at rt for 16 hours. Water (1 mL) was added and the reaction mixture was extracted with EtOAc (3×1 mL). The combined organic phases was washed with water (2×1 mL) and brine (1 mL) and then dried over $Na_2SO_4$, filtered and concentrated in vacuo. The pure compounds were obtained by redissolving the reaction mixture in DMSO followed by standard preparative HPLC purification.

Using this procedure the following compounds were obtained:

Example 9

Compound 109

2-(3,5-Dichloro-pyridin-4-yl)-1-{8-methoxy-2-[1-(morpholine-4-carbonyl)-cyclopropyl]-1,2,41-triazolo[1,5-a]pyridin-5-yl}-ethanone $^{13}$C NMR (DMSO-d$_6$) δ=186.3, 167.1, 165.0, 151.5, 147.2, 145.3, 140.4, 132.7, 128.5, 119.5, 106.8, 65.8, 56.8, 46.1, 44.2, 42.1, 24.4, 16.0
LC/MS: (m/z) 490.3 (MH+); RT=2.83 min; purity (UV)=100%
Amine: Morfoline

Example 10

Compound 110

1-{5-[2-(3,5-Dichloro-pyridin-4-yl)-acetyl]-8-methoxy-[1,2,4]triazolo[1,5-a]pyridin-2-yl}-cyclopropanecarboxylic acid benzylamide LC/MS: (m/z) 510.3 (MH+); RT=3.86 min; purity (UV)=94%
Amine: Benzylamine
1-{5-[2-(3,5-Dichloro-pyridin-4-yl)-acetyl]-8-methoxy-[1,2,4]triazolo[1,5-a]pyridin-2-yl}-cyclopropanecarboxylic acid benzylamide

Example 11

Compound 111

1-{5-[2-(3,5-Dichloro-pyridin-4-yl)-acetyl]-8-methoxy-[1,2,4]triazolo[1,5-a]pyridin-2-yl}-cyclopropanecarboxylic acid propylamide $^{13}$C NMR (DMSO-d$_6$) δ=186.3, 169.0, 164.3, 151.6, 147.2, 144.9, 140.6, 132.7, 128.5, 119.9, 106.8, 56.9, 44.1, 40.9, 23.6, 22.3, 17.4, 11.2
LC/MS: (m/z) 462.3 (MH+); RT=3.55 min; purity (UV)=94%
Amine: 1-Propylamine

Example 12

Compound 112

1-{5-[2-(3,5-Dichloro-pyridin-4-yl)-acetyl]-8-methoxy-[1,2,4]triazolo[1,5-a]pyridin-2-yl}-cyclopropanecarboxylic acid (pyridin-2-ylmethyl)-amide LC/MS: (m/z) 511.3 (MH+); RT=2.63 min; purity (UV)=100%
Amine: Pyridin-2-yl-methylamine

Example 13

Compound 113

1-{5-[2-(3,5-Dichloro-pyridin-4-yl)-acetyl]-8-methoxy-[1,2,4]triazolo[1,5-a]pyridin-2-yl}-cyclopropanecarboxylic acid (pyridin-3-ylmethyl)-amide
LC/MS: (m/z) 511.3 (MH+); RT=2.46 min; purity (UV)=89%

Amine: Pyridin-3-yl-methylamine

Example 14

Compound 114

1-{5-[2-(3,5-Dichloro-pyridin-4-yl)-acetyl]-8-methoxy-[1,2,4]triazolo[1,5-a]pyridin-2-yl}-cyclopropanecarboxylic acid (pyridin-4-ylmethyl)-amide LC/MS: (m/z) 511.3 (MH+); RT=2.35 min; purity (UV)=100%
Amine: Pyridin-4-yl-methylamine

Example 15

Compound 115

1-{5-[2-(3,5-Dichloro-pyridin-4-yl)-acetyl]-8-methoxy-[1,2,4]triazolo[1,5-a]pyridin-2-yl}-cyclopropanecarboxylic acid (2,2-dimethyl-propyl)-amide LC/MS: (m/z) 490.4 (MH+); RT=4.16 min; purity (UV)=100%
Amine: 2,2-Dimethyl-propylamine

Example 16

Compound 116

1-{5-[2-(3,5-Dichloro-pyridin-4-yl)-acetyl]-8-methoxy-[1,2,4]triazolo[1,5-a]pyridin-2-yl}-cyclopropanecarboxylic acid cyclopentylamide $^{13}$C NMR (DMSO-d$_6$) δ=186.1, 168.3, 164.4, 151.6, 147.2, 144.7, 140.5, 132.7, 128.3, 119.9, 106.8, 57.0, 50.8, 44.1, 32.2, 23.6, 23.3, 18.1
LC/MS: (m/z) 488.3 (MH+); RT=3.83 min; purity (UV)=100%
Amine: Cyclopentylamine

Example 17

Compound 117

1-{5-[2-(3,5-Dichloro-pyridin-4-yl)-acetyl]-8-methoxy-[1,2,4]triazolo[1,5-a]pyridin-2-yl}-cyclopropanecarboxylic acid isopropylamide $^{13}$C NMR (DMSO-d$_6$) δ=186.2, 167.9, 164.3, 151.6, 147.2, 144.8, 140.5, 132.7, 128.4, 119.8, 106.8, 56.9, 44.2, 40.9, 23.6, 22.2, 17.8
LC/MS: (m/z) 460.3 (MH+); RT=3.51 min; purity (UV)=100%
Amine: Isopropylamine

Example 18

Compound 118

1-{5-[2-(3,5-Dichloro-pyridin-4-yl)-acetyl]-8-methoxy-[1,2,4]triazolo[1,5-a]pyridin-2-yl}-cyclopropanecarboxylic acid amide

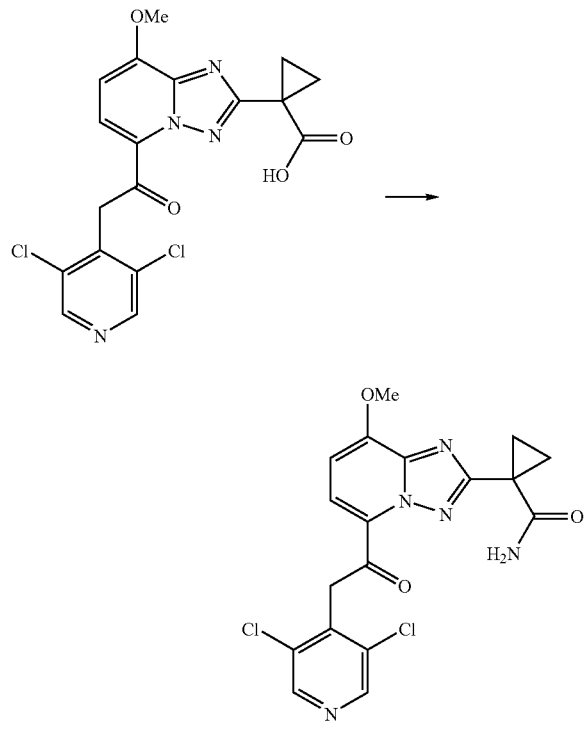 [SMILES: COc1ccc(C(=O)Cc2c(Cl)cncc2Cl)n2nc(C3(C(=O)O)CC3)nc12 ; COc1ccc(C(=O)Cc2c(Cl)cncc2Cl)n2nc(C3(C(N)=O)CC3)nc12]

Example 19

Compound 119

1-{2-[1-(Benzylamino-methyl)-cyclopropyl]-8-methoxy-[1,2,4]-triazolo[1,5-a]pyridin-5-yl}-2-(3,5-dichloro-pyridin-4-yl)-ethanone

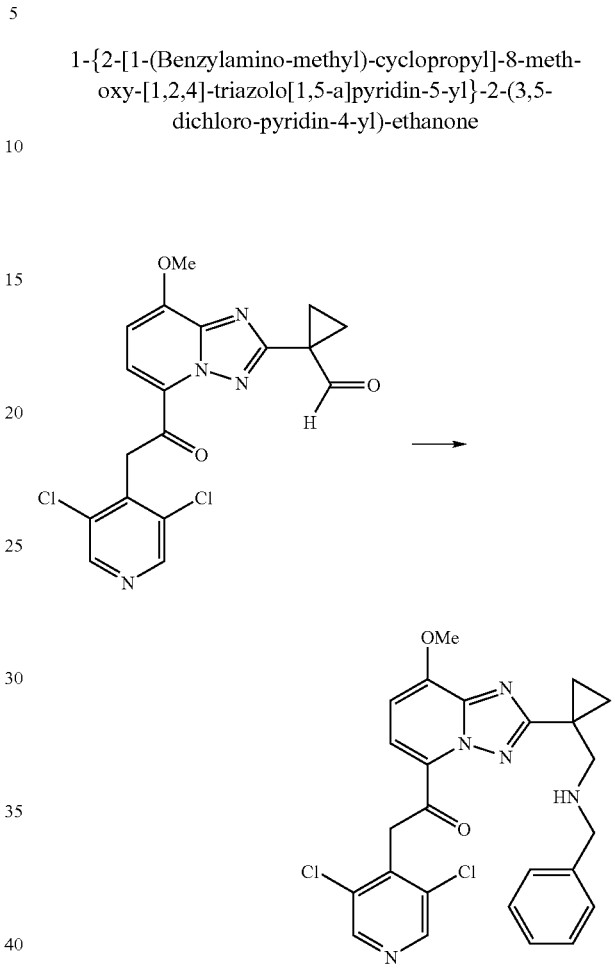

1-{5-[2-(3,5-Dichloro-pyridin-4-yl)-acetyl]-8-methoxy-[1,2,4]triazolo[1,5-a]pyridin-2-yl}-cyclopropanecarboxylic acid (0.05 mmol) obtained in example 8 was dissolved in DCM (0.2 mL) and one drop of DMF. Oxalyl chloride (0.0047 mL, 0.055 mmol) and the reaction mixture was left at rt for 1 hour. The solvent was removed in vacuo and the crude was redissolved in 1,4-dioxane (0.2 mL) and treated with ammonia (conc., 0.05 mL). The reaction mixture was left at rt for 4 hours and then evaporated in vacuo. $Na_2CO_3$ (sat. aq, 2 mL) was added and the organic products were extracted with DCM (3×2 mL). The combined organic phases were dried over $Na_2SO_4$, filtered and concentrated in vacuo to provide 19.7 mg crude compound. The pure compound was obtained by trituration of the crude with EtOAc. 13.6 mg pure product was obtained as a white solid.

$^{13}C$ NMR (DMSO-$d_6$) δ=186.4, 171.4, 164.6, 151.7, 147.3, 145.1, 140.8, 132.9, 128.5, 120.2, 106.9, 57.1, 43.9, 23.4, 17.9.

LC/MS: (m/z) 420.1 (MH+); RT=2.90 min; purity (UV)=100%

1-{5-[2-(3,5-Dichloro-pyridin-4-yl)-acetyl]-8-methoxy-[1,2,4]triazolo[1,5-a]pyridin-2-yl}-cyclopropanecarbaldehyde (14.2 mg, 0.035 mmol) obtained in preparation 12 was dissolved in MeOH (0.5 mL). Benzylamine (0.0042 mL, 0.038 mmol) was added followed by sodium cyanoborohydride (3.2 mg, 0.049 mmol). The reaction mixture was left at rt for 18 hours and then concentrated in vacuo. The crude was mixed with brine (1 mL) and two drops of NaOH (aq. 2N) and then extracted with DCM (3×1 mL). The combined organic phases were dried over $Na_2SO_4$, filtered and concentrated in vacuo. The product was purified by flash chromatography using DCM-MeOH—$NH_4OH$ (99:1:0.1% to 95:5:0.1%) as eluent to provide 5.3 mg of the desired product as a colourless solid.

$^{13}C$ NMR (CDCl$_3$) δ=186.4, 169.2, 151.9, 147.3, 145.9, 140.6, 140.3, 133.5, 129.4, 128.2, 127.9, 126.8, 118.9, 105.3, 56.8, 54.7, 53.9, 45.3, 20.2, 15.8

LC/MS: (m/z) 496.3 (MH+); RT=2.77 min; purity (UV)=100%

General Procedure for Preparation of Compounds of Formula Id, Wherein HetAr is as Defined Above:

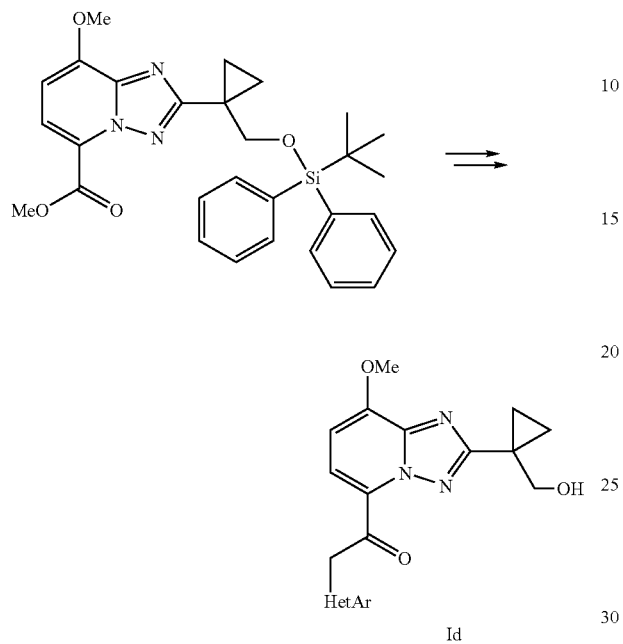

2-[1-(tert-Butyl-diphenyl-silanyloxymethyl)-cyclopropyl]-8-methoxy-[1,2,4]triazolo[1,5-a]pyridine-5-carboxylic acid methyl ester (38.3 mg, 0.074 mmol) obtained from Preparation 11 and a HetAr-Me compound (0.089 mmol, see below) was dissolved in dry THF (1 mL) under argon. The mixture was cooled to 0° and treated dropwise with LiHMDS (0.15 mL of a 1M solution). The reaction mixture was brought to room temperature and left overnight. The reaction was quenched with NH$_4$Cl (sat., 2 mL) and the organic products were extracted with DCM (2×2 mL). The combined organic phases were dried over Na$_2$SO$_4$ and evaporated in vacuo. The crude was redissolved in diethyl ether (0.8 mL) and treated with acetyl chloride (0.1 mL) in MeOH (1.4 mL) for 16 hours at rt. NaHCO$_3$ (aq. sat, 1.5 mL) was added and the reaction mixture was extracted with DCM (2 mL). The organic phase was dried over Na$_2$SO$_4$, filtered and concentrated in vacuo. The pure compounds were obtained by redissolving the reaction mixture in DMSO followed by standard preparative HPLC purification.

Using this procedure the following compounds were obtained:

Example 20

Compound 120

1-[2-(1-Hydroxymethyl-cyclopropyl)-8-methoxy-[1,2,4]triazolo[1,5-a]pyridin-5-yl]-2-pyrazin-2-yl-ethanone LC/MS: (m/z) 340.3 (MH+); RT=1.98+2.78 min due to keton-enol tautomers; purity (UV)=100%

Example 21

Compound 121

1-[2-(1-Hydroxymethyl-cyclopropyl)-8-methoxy-[1,2,4]triazolo[1,5-a]pyridin-5-yl]-2-quinolin-4-yl-ethanone LC/MS: (m/z) 389.4 (MH+); RT=2.03 min; purity (UV)=100%

Example 22

Compound 122

1-[2-(1-Hydroxymethyl-cyclopropyl)-8-methoxy-[1,2,4]triazolo[1,5-a]pyridin-5-yl]-2-pyridin-4-yl-ethanone LC/MS: (m/z) 339.3 (MH+); RT=1.54 min; purity (UV)=83%

Example 23

Compound 123

2-(3,5-Dibromo-pyridin-4-yl)-1-[2-(1-hydroxymethyl-cyclopropyl)-8-methoxy-[1,2,4]triazolo[1,5-a]pyridin-5-yl]-ethanone $^{13}$C NMR (DMSO-d$_6$) δ=186.6, 167.8, 151.6, 150.2, 145.4, 144.2, 128.7, 124.1, 119.3, 106.5, 63.1, 56.9, 49.8, 21.9, 13.0

LC/MS: (m/z) 497.1 (MH+); RT=3.13 min; purity (UV)=100%

Example 24

Compound 124

2-(3-Bromo-pyridin-4-yl)-1-[2-(1-hydroxymethyl-cyclopropyl)-8-methoxy-[1,2,4]triazolo[1,5-a]pyridin-5-yl]-ethanone LC/MS: (m/z) 417.2 (MH+); RT=2.55 min; purity (UV)=100%

Example 25

Compound 125

4-{2-[2-(1-Hydroxymethyl-cyclopropyl)-8-methoxy-[1,2,4]triazolo[1,5-a]pyridin-5-yl]-2-oxo-ethyl}-pyridine-2-carbonitrile LC/MS: (m/z) 364.3 (MH+); RT=2.49 min; purity (UV)=92%

Example 26

Compound 126

2-(3-Chloro-pyrazin-2-yl)-1-[2-(1-hydroxymethyl-cyclopropyl)-8-methoxy-[1,2,4]triazolo[1,5-a]pyridin-5-yl]-ethanone LC/MS: (m/z) 374.2 (MH+); RT=2.56+3.32 min due to keton-enol tautomers; purity (UV)=100%

Example 27

Compound 127

2-(2-Chloro-phenyl)-1-(2-cyclopropyl-8-methoxy-[1,2,4]triazolo[1,5-a]pyridin-5-yl)-ethanone

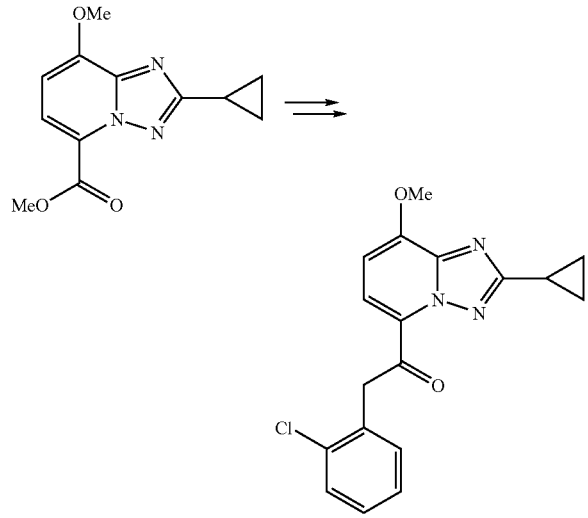

2-Cyclopropyl-8-methoxy-[1,2,4]triazolo[1,5-a]pyridine-5-carboxylic acid methyl ester (24.7 mg, 0.1 mmol) obtained from preparation 5 was dissolved in dry THF (0.25 mL) under argon. The mixture was cooled to −10° and treated dropwise with 2-chlorobenzylmagnesium chloride (0.375 mL of a 0.25M solution). The reaction mixture was stirred for 15 min and then brought to room temperature and left for 1½ hours. The reaction was cooled to −10° and quenched with NH$_4$Cl (sat., 0.2 mL) and water (1 mL) and the organic products were extracted with DCM (3×2 mL). The combined organic phases were dried over Na$_2$SO$_4$ and evaporated in vacuo. The product was purified by flash chromatography on silica using EtOAc (2 to 4%) in heptane as eluent to provide 9.8 mg of the desired compound as a white solid.

$^{13}$C NMR (CDCl$_3$) δ=190.0, 168.3, 151.3, 134.7, 133.1, 131.9, 130.1, 129.4, 128.6, 126.8, 118.1, 105.1, 56.6, 47.8, 9.5, 9.2

LC/MS: (m/z) 340.3 (MH+); RT=4.03 min; purity (UV)=100%

Example 28

Compound 128

1-(2-Cyclopropyl-8-methoxy-[1,2,4]triazolo[1,5-a]pyridin-5-yl)-2-(3,5-dichloro-1-oxy-pyridin-4-yl)-ethanone

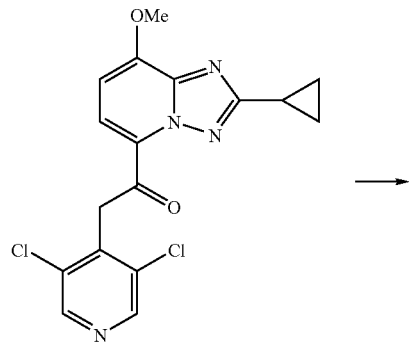

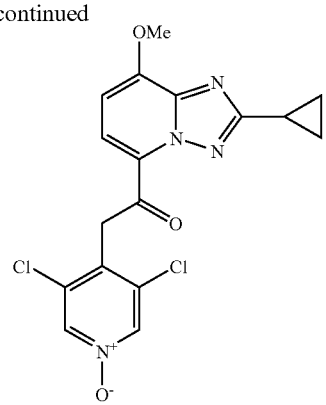

1-(2-Cyclopropyl-8-methoxy-[1,2,4]triazolo[1,5-a]pyridin-5-yl)-2-(3,5-dichloro-pyridin-4-yl)-ethanone (12.3 mg, 0.033 mmol) obtained in example 1 was dissolved in dry DCM (0.25 mL). Methyltrioxorhenium (4.1 mg, 0.016 mmol) was added followed by hydrogenperoxide (0.002 mL, 0.066 mmol) and the reaction mixture was stirred at rt overnight. MnO$_2$ (0.8 mg, 0.009 mmol) was added. After 2 minutes the reaction mixture was filtered and the reaction mixture was evaporated in vacuo. The crude was re-dissolved in DMSO (0.4 mL). The pure product was obtained by standard preparative HPLC purification.

$^{13}$C NMR (CDCl$_3$) δ=186.4, 168.5, 152.0, 145.9, 137.5, 134.3, 131.5, 129.0, 118.9, 105.2, 56.8, 44.7, 9.5, 9.4

Example 29

PDE4 Assay

Human recombinant PDE4 (Gene bank accession no NM_006203) was incubated for 1 hour with the test compound at concentrations up to 10 μM, with cAMP (1×10-5M), and with a low amount (0.021 MBq) of radioactively labelled cAMP. At the end of the incubation, the cleavage of the substrate was evaluated by the binding of the AMP product to SPA beads, which generate chemo luminescence when bound to the radioactive tracer. The AMP product inhibited the binding of the radioactive tracer to the beads, and the luminescent signal was competed. The results were calculated as the molar concentrations resulting in 50% inhibition of the substrate cleavage compared to controls samples, and are expressed as IC$_{50}$ (nM) in the table below.

Example 30

TNFα Release

Human peripheral blood mononuclear cells (PBMC) were isolated from buffy coats. The blood was mixed with saline at a ratio of 1:1, and the PBMC were isolated by the use of Lymphoprep Tubes™ (Nycomed, Norway). The PBMC were suspended in RPMI1640 with 2% foetal calf serum (FCS), pen/strep and 2 mM L-glutamine at a concentration of 5×105 c/ml. The cells were pre-incubated for 30 minutes with the test compounds in 96 well tissue culture plates and stimulated for 18 hours with lipopolysaccharide 1 mg/ml (Sigma). The level of TNFα was measured in the culture supernatant by enzyme immuno assays using primary and secondary biotinylated antibodies from R&D systems. The results shown in the table below are expressed as IC$_{50}$ values calculated from inhibition curves using as positive controls the secretion in LPS stimulated wells and as negative controls the secretion in unstimulated cells.

| Example | Compound | | PDE4 IC50 (nM) | TNFa IC50 (nM) |
|---|---|---|---|---|
| Example 1 | 101 | (structure) | 2 | 3 |
| Example 2 | 102 | (structure) | 134 | 291 |
| Example 3 | 103 | (structure) | 7 | 27 |
| Example 4 | 104 | (structure) | 26 | 66 |

-continued

| Example | Compound | | PDE4 IC50 (nM) | TNFa IC50 (nM) |
|---|---|---|---|---|
| Example 5 | 105 | (structure) | 305 | 603 |
| Example 6 | 106 | (structure) | 4 | 5 |
| Example 7 | 107 | (structure) | 45 | 117 |
| Example 8 | 108 | (structure) | 55 | ND |

-continued
| Example | Compound | | PDE4 IC50 (nM) | TNFa IC50 (nM) |
|---|---|---|---|---|
| Example 9 | 109 | 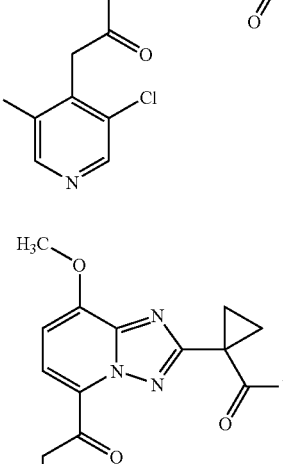 | 24 | 29 |
| Example 10 | 110 | 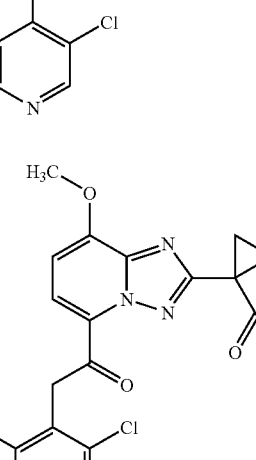 | 0.5 | 0.7 |
| Example 11 | 111 | 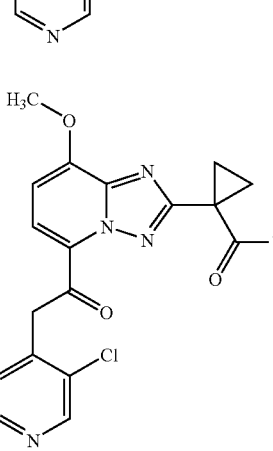 | 0.3 | 0.3 |
| Example 12 | 112 |  | 1 | 0.6 |

-continued
| Example | Compound | | PDE4 IC50 (nM) | TNFa IC50 (nM) |
|---|---|---|---|---|
| Example 13 | 113 | 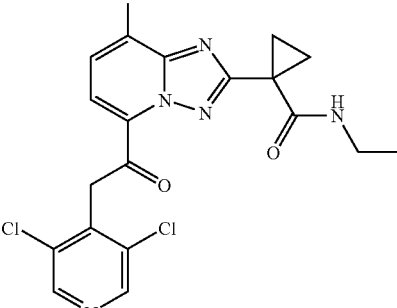 | 0.7 | 0.5 |
| Example 14 | 114 | 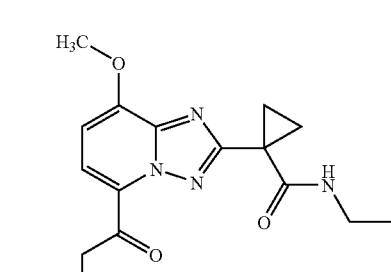 | 0.4 | 0.2 |
| Example 15 | 115 | 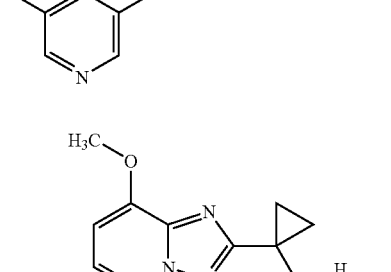 | 0.2 | 0.2 |
| Example 16 | 116 | 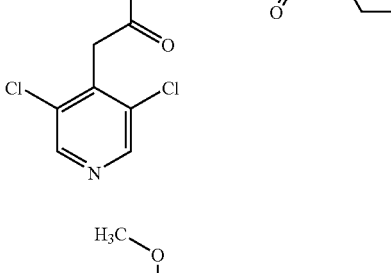 | 0.1 | ND |

-continued
| Example | Compound | | PDE4 IC50 (nM) | TNFa IC50 (nM) |
|---|---|---|---|---|
| Example 17 | 117 | 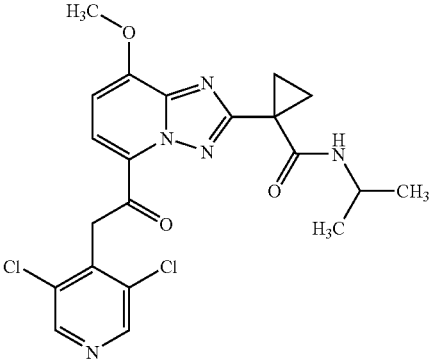 [SMILES: COc1ccc(C(=O)Cc2c(Cl)cncc2Cl)n2nc(C3(C(=O)NC(C)C)CC3)nc12] | 0.2 | 0.2 |
| Example 18 | 118 | 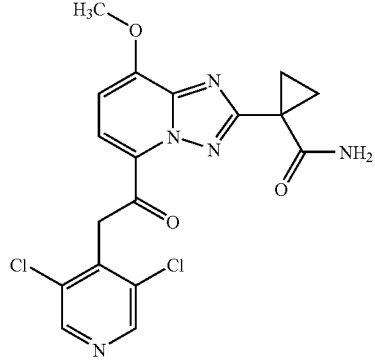 [SMILES: COc1ccc(C(=O)Cc2c(Cl)cncc2Cl)n2nc(C3(C(N)=O)CC3)nc12] | 3 | 2 |
| Example 19 | 119 | 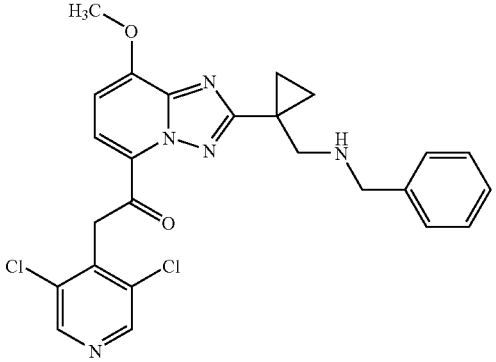 [SMILES: COc1ccc(C(=O)Cc2c(Cl)cncc2Cl)n2nc(C3(CNCc4ccccc4)CC3)nc12] | 8 | 13 |
| Example 20 | 120 | 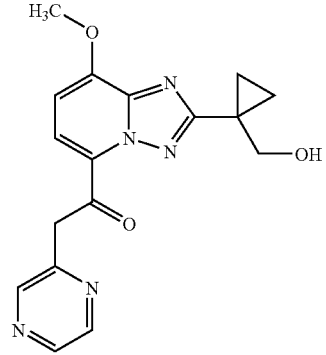 [SMILES: COc1ccc(C(=O)Cc2cnccn2)n2nc(C3(CO)CC3)nc12] | 2500 | 2200 |

-continued

| Example | Compound | | PDE4 IC50 (nM) | TNFa IC50 (nM) |
|---|---|---|---|---|
| Example 21 | 121 | [structure] | 3600 | 2100 |
| Example 22 | 122 | [structure] | 261 | 139 |
| Example 23 | 123 | [structure] | 68 | 15 |
| Example 24 | 124 | [structure] | 52 | 115 |

-continued

| Example | Compound | | PDE4 IC50 (nM) | TNFa IC50 (nM) |
|---|---|---|---|---|
| Example 25 | 125 | (structure) | 3100 | 4800 |
| Example 26 | 126 | (structure) | 548 | 712 |
| Example 27 | 127 | (structure) | 46 | 105 |
| Example 28 | 128 | (structure) | 3 | 5 |

The invention claimed is:
1. A compound according to formula I,

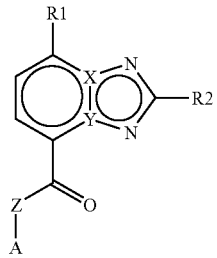

wherein
$R_1$ is halogen, or $R_1$ is alkyl, alkenyl, alkynyl, haloalkyl, alkoxy, cycloalkyl, alkoxycarbonyl, aryl, each being optionally substituted with one or more substituents selected from $R_3$;
$R_2$ is substituted cycloalkyl being substituted with one or more substituents selected from $R_4$;
$R_3$ is hydrogen, aryl, heteroaryl, oxo, halogen, hydroxy, alkyl, cycloalkyl, alkoxy, or amino;
$R_4$ is halogen, oxo, hydroxy, carboxy, alkyl, alkoxy, amino, —$NR_aR_b$ or —C(O)—$NR_aR_b$, wherein each of $R_a$ and $R_b$ is independently hydrogen, hydroxy, alkyl, alkenyl, aryl, cycloalkyl, heterocycloalkyl, heteroaryl, alkylaryl or alkylheteroaryl, or $R_a$ and $R_b$ together with the nitrogen atom to which they are attached form a heterocycloalkyl ring, each being optionally substituted with one or more substituents selected from $R_3$, or $R_4$ is aryl substituted with one or more substituents selected from $R_5$;
X and Y are either C and N or N and C, respectively;
Z is —$CH_2$—;
A is aryl, cycloalkyl, cycloalkenyl, heteroaryl, heterocycloalkyl or heterocycloalkenyl, each being optionally substituted with one or more substituents selected from the group consisting of $R_5$;
$R_5$ is hydrogen, halogen, oxo, alkyl or alkoxy;
and pharmaceutically acceptable salts and N-oxides thereof.

2. A compound according to claim 1, wherein A is optionally substituted heteroaryl.
3. A compound according to claim 1 or 2, wherein A is optionally substituted pyridyl.
4. A compound according to claim 1, wherein A is substituted with one or more substituents selected from chlorine, fluorine, or bromine.
5. A compound according to claim 1, wherein A is 4-(3,5-dichloropyridyl).
6. A compound according to claim 1, wherein $R_1$ is $C_{1-6}$ alkoxy or halogen.
7. A compound according to claim 1, wherein $R_1$ is methoxy.
8. A compound according to claim 1, of general formula Ia Ia

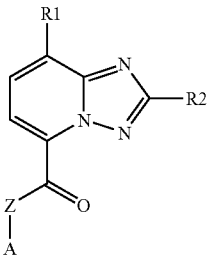

wherein $R_1$, $R_2$, Z and A are as defined in claim 1.

9. A compound according to claim 1, wherein $R_2$ is substituted cyclopropyl.
10. A compound according to claim 1, wherein $R_4$ is —C(O)—$NR_aR_b$, wherein $R_a$ and $R_b$ are both hydrogen, or one of $R_a$ and $R_b$ is hydrogen and the other is hydroxy, alkyl, alkenyl, aryl, cycloalkyl, heterocycloalkyl, heteroaryl, alkylaryl or alkylheteroaryl, or $R_a$ and $R_b$ together with the nitrogen atom to which they are attached form a heterocycloalkyl ring.
11. A compound according to claim 1 selected from the group consisting of
1-{5-[2-(3,5-Dichloro-pyridin-4-yl)-acetyl]-8-methoxy-[1,2,4]triazolo[1,5-a]pyridin-2-yl}-cyclopropanecarboxylic acid (compound 108),
2-(3,5-Dichloro-pyridin-4-yl)-1-{8-methoxy-2-[1-(morpholine-4-carbonyl)-cyclopropyl]-[1,2,4]triazolo[1,5-a]pyridin-5-yl}-ethanone (compound 109),
1-{5-[2-(3,5-Dichloro-pyridin-4-yl)-acetyl]-8-methoxy-[1,2,4]triazolo[1,5-a]pyridin-2-yl}-cyclopropanecarboxylic acid benzylamide (compound 110),
1-{5-[2-(3,5-Dichloro-pyridin-4-yl)-acetyl]-8-methoxy-[1,2,4]triazolo[1,5-a]pyridin-2-yl}-cyclopropanecarboxylic acid propylamide (compound 111),
1-{5-[2-(3,5-Dichloro-pyridin-4-yl)-acetyl]-8-methoxy-[1,2,4]triazolo[1,5-a]pyridin-2-yl}-cyclopropanecarboxylic acid (pyridin-2-ylmethyl)-amide (compound 112),
1-{5-[2-(3,5-Dichloro-pyridin-4-yl)-acetyl]-8-methoxy-[1,2,4]triazolo[1,5-a]pyridin-2-yl}-cyclopropanecarboxylic acid (pyridin-3-ylmethyl)-amide (compound 113),
1-{5-[2-(3,5-Dichloro-pyridin-4-yl)-acetyl]-8-methoxy-[1,2,4]triazolo[1,5-a]pyridin-2-yl}-cyclopropanecarboxylic acid (pyridin-4-ylmethyl)-amide (compound 114),
1-{5-[2-(3,5-Dichloro-pyridin-4-yl)-acetyl]-8-methoxy-[1,2,4]triazolo[1,5-a]pyridin-2-yl}-cyclopropanecarboxylic acid (2,2-dimethyl-propyl)-amide (compound 115),
1-{5-[2-(3,5-Dichloro-pyridin-4-yl)-acetyl]-8-methoxy-[1,2,4]triazolo[1,5-a]pyridin-2-yl}-cyclopropanecarboxylic acid cyclopentylamide (compound 116),
1-{5-[2-(3,5-Dichloro-pyridin-4-yl)-acetyl]-8-methoxy-[1,2,4]triazolo[1,5-a]pyridin-2-yl}-cyclopropanecarboxylic acid isopropylamide (compound 117),
1-{5-[2-(3,5-Dichloro-pyridin-4-yl)-acetyl]-8-methoxy-[1,2,4]triazolo[1,5-a]pyridin-2-yl}-cyclopropanecarboxylic acid amide (compound 118),
and pharmaceutically acceptable salts and N-oxides thereof.

12. A pharmaceutical composition comprising a compound according to claim 1 together with a pharmaceutically acceptable vehicle or excipient or pharmaceutically acceptable carrier(s).
13. A pharmaceutical composition according to claim 12 further comprising one or more other therapeutically active compound(s).

* * * * *